(12) United States Patent
Wakasa et al.

(10) Patent No.: US 8,673,597 B2
(45) Date of Patent: Mar. 18, 2014

(54) METHOD FOR PRODUCING L-AMINO ACID

(75) Inventors: Yuori Wakasa, Kawasaki (JP); Ryo Takeshita, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/114,251

(22) Filed: May 24, 2011

(65) Prior Publication Data

US 2011/0281311 A1 Nov. 17, 2011

Related U.S. Application Data

(63) Continuation of application No. PCT/JP2009/069956, filed on Nov. 26, 2009.

(30) Foreign Application Priority Data

Nov. 27, 2008 (JP) ................................. 2008-302521

(51) Int. Cl.
C12P 13/04 (2006.01)
C12P 13/20 (2006.01)
C12P 13/12 (2006.01)
C12P 13/08 (2006.01)
C12P 13/06 (2006.01)

(52) U.S. Cl.
USPC ........... 435/106; 435/109; 435/113; 435/115; 435/116

(58) Field of Classification Search
None
See application file for complete search history.

(56) References Cited

U.S. PATENT DOCUMENTS

| | | | |
|---|---|---|---|
| 5,175,107 A | 12/1992 | Debabov et al. | |
| 5,661,012 A | 8/1997 | Sano et al. | |
| 5,688,671 A | 11/1997 | Sugimoto et al. | |
| 5,827,698 A | 10/1998 | Kikuchi et al. | |
| 5,830,716 A | 11/1998 | Kojima et al. | |
| 5,932,453 A | 8/1999 | Kikuchi et al. | |
| 6,040,160 A | 3/2000 | Kojima et al. | |
| 6,132,999 A | 10/2000 | Debabov et al. | |
| 6,303,348 B1 | 10/2001 | Livshits et al. | |
| 6,319,696 B1 | 11/2001 | Kishino et al. | |
| 7,186,531 B2 | 3/2007 | Akhverdian et al. | |
| 7,306,933 B2 | 12/2007 | Dien et al. | |
| 7,790,422 B2 | 9/2010 | Takeshita et al. | |
| 7,833,762 B2 | 11/2010 | Kataoka et al. | |
| 2002/0025564 A1 | 2/2002 | Kobayashi et al. | |
| 2002/0110876 A1 | 8/2002 | Miyata et al. | |
| 2002/0160461 A1 | 10/2002 | Nakai et al. | |
| 2004/0132165 A1 | 7/2004 | Akhverdian et al. | |
| 2005/0239177 A1 | 10/2005 | Livshits et al. | |
| 2006/0019355 A1 | 1/2006 | Ueda et al. | |
| 2006/0088919 A1 | 4/2006 | Rybak et al. | |
| 2006/0216796 A1 | 9/2006 | Hashiguchi et al. | |
| 2007/0004014 A1 | 1/2007 | Tsuji et al. | |
| 2007/0243590 A1 | 10/2007 | Takeshita et al. | |
| 2009/0215130 A1 | 8/2009 | Iyo et al. | |
| 2009/0239269 A1 | 9/2009 | Tajima et al. | |
| 2009/0258401 A1 | 10/2009 | Iyo et al. | |
| 2010/0273221 A1 | 10/2010 | Takeshita et al. | |
| 2011/0003347 A1 | 1/2011 | Takeshita et al. | |

FOREIGN PATENT DOCUMENTS

| | | |
|---|---|---|
| EP | 1038970 | 9/2000 |
| JP | 05-276935 | 10/1993 |
| JP | 2002-065287 | 3/2002 |
| JP | 2005-237379 | 9/2005 |
| WO | WO01/53459 | 7/2001 |
| WO | WO2006/038695 | 4/2006 |
| WO | WO2008/044453 | 4/2008 |

OTHER PUBLICATIONS

Branden et al., "Introduction to Protein Structure Second Edition", Garland Publishing Inc., New York, 1999.*
Witkowski et al., Biochemistry, 38, 11643-11650, 1999.*
Wishart et al., Journal of Biological Chemistry, vol. 270, No. 45, pp. 26782-26785, 1995.*
Kisselev, Structure, vol. 10, pp: 8-9, 2002.*
Deguchi, Y. et al., "Molecular Cloning of gltS and gltP, Which Encode Glutamate Carriers of *Escherichia coli* B," J. Bacteriol. 1989;171(3):1314-1319.
Deguchi, Y., et al., "Nucleotide Sequence of *gltS*, the Na$^+$/Glutamate Symport Carrier Gene of *Escherichia coli* B," J. Biol. Chem. 1990;265(35):21704-21708.
Hasegawa, K., et al., "Isolation and Purification Technology in Fermentation Industry of Amino Acids," Bioscience and Industry, Mar. 2008, vol. 66, No. 3, pp. 124-129 with partial English translation thereof.
Tolner, B., et al., "Revised Nucleotide Sequence of the *gltP* Gene, Which Encodes the Proton-Glutamate-Aspartate Transport Protein of *Escherichia coli* K-12," J. Bacteriol. 1992;174(7):2391-2393.
Trötschel, C., et al., "GltS, the sodium-coupled L-glutamate uptake system of *Corynebacterium glutamicum*: identification of the corresponding gene and impact of L-glutamate production," Appl. Microbiol. Biotechnol. 2003;60:738-742.
Wallace, B., et al., "Cloning and Sequencing of a Gene Encoding a Glutamate and Aspartate Carrier of *Escherichia coli* K-12," J. Bacteriol. 1990;172(6):3214-3220.
International Search Report for PCT Patent App. No. PCT/JP2009/069956 (Jan. 26, 2010).
Booth, I. R., et al., "A Genetic Locus for the GltII-Glutamate Transport System in *Escherichia coli*." J. Gen. Microbiol. 1989;135:2767-2774.
Dobrowolski, A., et al., "Membrane Topology Prediction by Hydropathy Profile Alignment: Membrane Topology of the Na$^+$-Glutamate Transporter GltS," Biochem. 2007;46:2326-2332.

(Continued)

Primary Examiner — Suzanne M Noakes
Assistant Examiner — Jae W Lee
(74) Attorney, Agent, or Firm — Shelly Guest Cermak; Cermak Nakajima LLP

(57) ABSTRACT

A bacterium which belongs to the family Enterobacteriaceae, and has an ability to produce L-lysine, L-threonine, L-asparagine, L-aspartic acid, L-methionine, L-alanine, L-isoleucine, and/or L-homoserine. The bacterium has been modified so that expression of the gltP and/or gltS genes is/are increased when cultured in a medium, resulting in the accumulation of the L-amino acid(s) in the medium or bacterial cells.

13 Claims, No Drawings

(56) References Cited

OTHER PUBLICATIONS

Deguchi, Y., et al., "Molecular Cloning of *gltS* and *gltP*, Which Encode Glutamate Carriers of *Escherichia coli* B," J. Bacteriol. 1989;171(3):1314-1319.

Jacobs, M. H. J., et al., "Expression of the *gltP* gene of *Escherichia coli* in a glutamate transport-deficient mutant of *Rhodobacter sphaeroides* restores chemotaxis to glutamate," Mol. Microbiol. 1995;18(4):641-647.

Kalman, M., et al., "Characterization of the *Escherichia coli* K12 *gltS* glutamate permease gene," Mol. Gen. Genet. 1991;225:379-386.

Raunser, S., et al., "Structure and Function of Prokaryotic Glutamate Transporters from *Escherichia coli* and *Pyrococcus horikoshii*," Biochem. 2006;45:12796-12805.

Szvetnik, A., et al., "Membrane topology of the GltS $Na^+$/glutamate permease of *Escherichia coli*," FEMS Microbiol. Lett. 2007;275:71-79.

Tolner, B., et al., "Cation-selectivity of the L-glutamate transporters of *Escherichia coli*, *Bacillus stearothermophilus* and *Bacillus caldotenax*: dependence on the environment in which the proteins are expressed," Mol. Microbiol. 1995;18(1):123-133.

Tolner, B., et al., "Characterization of the Proton/Glutamate Symport Protein of *Bacillus subtilis* and Its Functional Expression in *Escherichia coli*," J. Bacteriol. 1995;177(10):2863-2869.

Tramonti, A., et al., "Mechanisms of Transcription Activation Exerted by GadX and GadW at the *gadA* and *gadBC* Gene Promoters of the Glutamate-Based Acid Resistance System in *Escherichia coli*," J. Bacteriol. 2006;188(23):8118-8127.

Trötschel, C., et al., "GltS, the sodium-coupled L-glutamate uptake system of *Corynebacterium glutamicum*: identification of the corresponding gene and impact on L-glutamate production," Appl. Microbiol. Biotechnol. 2003;60:738-742.

International Preliminary Report on Patentability and Written Opinion for PCT Patent App. No. PCT/JP2009/069956 (Jul. 5, 2011).

Burkovski, A., et al., "Functional expression of the glutamate uptake system from *Corynebacterium glutamicum* in *Escherichia coli*," FEMS Microbiol. Lett. 1995;127:263-266.

Motter, A. E., et al., "Predicting synthetic rescues in metabolic networks," Mol. Sys. Biol. 2008;4(168):1-10.

Supplementary European Search Report for EP Patent App. No. 09829135.4 (Jul. 13, 2012).

* cited by examiner

METHOD FOR PRODUCING L-AMINO ACID

This application is a Continuation of, and claims priority under 35 U.S.C. §120 to, International Application No. PCT/JP2009/069956, filed Nov. 26, 2009, and claims priority therethrough under 35 U.S.C. §119 to Japanese Patent Application No. 2008-302521, filed Nov. 27, 2008, the entireties of which are incorporated by reference herein. Also, the Sequence Listing filed electronically herewith is hereby incorporated by reference (File name: 2011-05-24T_US-462_Seq_List; File size: 43 KB; Date recorded: May 24, 2011).

BACKGROUND OF THE INVENTION

1. Technical Field

The present invention relates to a method for producing an L-amino acid using a bacterium. L-amino acids are industrially useful as animal feed additives, health food ingredients, amino acid infusions, and so forth.

2. Background Art

Methods for producing a target substance such as an L-amino acid by fermentation include using a microorganism such as a wild-type microorganism (a wild-type strain), an auxotrophic strain derived from a wild-type strain, a metabolic regulation mutant strain derived from a wild-type strain that may be resistant to various drugs, a strain having properties of both an auxotrophic strain and metabolic regulation mutant strain, and so forth.

In recent years, recombinant DNA techniques have been used in the production of target substances by fermentation. For example, L-amino acid productivity by a microorganism can be improved by increasing expression of a gene encoding an L-amino acid biosynthetic enzyme (U.S. Pat. Nos. 5,168,056 and 5,779,736), or by increasing uptake of a carbon source into the L-amino acid biosynthesis system (U.S. Pat. No. 5,906,925).

Use of carbonate and bicarbonate ions as counter anions to basic amino acids have been disclosed in a method of production of basic amino acids instead of sulfate or chloride ions. The disclosed methods include adding carbonate ions and bicarbonate ions to the medium, controlling the internal pressure of the fermentation tank so that it is positive during the fermentation, or supplying carbon dioxide or a mixed gas containing carbon dioxide to the medium (U.S. Patent Published Application No. 2002/0025564, WO2006/038695).

Conventional amino acid fermentation for members of the L-aspartic acid family, such as L-lysine, is accompanied by the by-production of L-glutamic acid, and in particular, is made even worse by a high pH of the fermentation medium. Since it is often necessary to purify L-amino acids to a high purity level after fermentative production, the presence of by-products is often a problem, and can complicate the purification process ultimately resulting in a reduction of the purity of the desired product.

To date, proteins involved in the uptake of glutamic acid which have been reported in enterobacteria such as *Escherichia coli* include GltP, GltS (J. Bacteriol., 1992 April; 174 (7):2391-3, J. Biol. Chem., 1990 December; 15; 265 (35): 21704-8), GadC (J. Bacteriol., 2006 December; 188 (23): 8118-27), and GltIJKL.

It is known that production of L-lysine, L-threonine and L-tryptophan by a strain that has been modified so that the glutamate decarboxylase activity is enhanced can be improved by enhancing the glutamate/GABA anti-porter activity (WO2008/044453). However, there have been no reports of production of L-amino acid using a microorganism in which the gltP and/or gltS genes is/are amplified.

SUMMARY OF THE INVENTION

The present invention provides a microorganism belonging to the family Enterobacteriaceae that can reduce production of L-glutamic acid as a by-product in the production of an amino acid such as L-lysine, L-threonine, L-asparagine, L-aspartic acid, L-methionine, L-alanine, L-isoleucine, and L-homoserine, and a method for producing such an L-amino acid as described above by using such a microorganism as described above, which can reduce L-glutamic acid which is produced as a by-product in the production of the amino acid.

It was found that L-glutamic acid was produced as a by-product during fermentative production of L-amino acids, and that the amount of L-glutamic acid could be reduced by modifying a bacterium so that expression of gltP or/and gltS is increased.

It is an aspect of the present invention to provide a method for producing an L-amino acid comprising culturing a bacterium in a medium, wherein said bacterium belongs to the family Enterobacteriaceae and is able to produce an L-amino acid, and collecting the L-amino acid from the medium, wherein the bacterium has been modified so that expression of a gltP and/or gltS gene(s) is/are increased, and the L-amino acid is selected from the group consisting of L-lysine, L-threonine, L-asparagine, L-aspartic acid, L-methionine, L-alanine, L-isoleucine, and L-homoserine.

It is a further aspect of the present invention to provide the method as described above, wherein the gltP gene encodes a protein selected from the group consisting of:

(A) a protein comprising the amino acid sequence shown in SEQ ID NO: 12, and (B) a protein comprising the amino acid sequence shown in SEQ ID NO: 12, but wherein one or several amino acid residues are substituted, deleted, inserted, added or inverted, and said protein has an L-glutamate transporter activity.

It is a further aspect of the present invention to provide the method as described above, wherein the gltP gene encodes a protein selected from the group consisting of:

(A) a protein comprising the amino acid sequence shown in SEQ ID NO: 2, and (B) a protein comprising the amino acid sequence shown in SEQ ID NO: 2, but wherein one or several amino acid residues are substituted, deleted, inserted, added or inverted, and said protein has an L-glutamate transporter activity.

It is a further aspect of the present invention to provide the method as described above, wherein the gltP gene is a DNA selected from the group consisting of:

(A) a DNA comprising the nucleotide sequence shown in SEQ ID NO: 1, and (B) a DNA which is able to hybridize with a sequence complementary to the nucleotide sequence shown in SEQ ID NO: 1, or a probe which can be prepared from the nucleotide sequence, under stringent conditions, and encodes a protein having an L-glutamate transporter activity.

It is a further aspect of the present invention to provide the method as described above, wherein the gltS gene encodes a protein selected from the group consisting of (A) a protein comprising the amino acid sequence shown in SEQ ID NO: 13, and (B) a protein comprising the amino acid sequence shown in SEQ ID NO: 13, but wherein one or several amino acid residues are substituted, deleted, inserted, added or inverted, and said protein has an L-glutamate transporter activity.

It is a further aspect of the present invention to provide the method as described above, wherein the gltS gene encodes a protein selected from the group consisting of:

(A) a protein comprising the amino acid sequence shown in SEQ ID NO: 4, and (B) a protein comprising the amino acid sequence shown in SEQ ID NO: 4, but wherein one or several amino acid residues are substituted, deleted, inserted, added or inverted, and said protein has an L-glutamate transporter activity.

It is a further aspect of the present invention to provide the method as described above, wherein the gltS gene is a DNA selected from the group consisting of:

(A) a DNA comprising the nucleotide sequence shown in SEQ ID NO: 3, and (B) a DNA which is able to hybridize with a sequence complementary to the nucleotide sequence shown in SEQ ID NO: 3, or a probe which can be prepared from the nucleotide sequence, under stringent conditions, and encodes a protein having an L-glutamate transporter activity.

It is a further aspect of the present invention to provide the method as described above, wherein expression of the gene is enhanced by increasing copy number of the gene, or by modifying an expression control sequence of the gene.

It is a further aspect of the present invention to provide the method as described above, wherein the L-amino acid is L-lysine, and expression of ybjE gene is increased in the bacterium.

It is a further aspect of the present invention to provide the method as described above, wherein the ybjE gene encodes a protein selected from the group consisting of:

(A) a protein comprising the amino acid sequence shown in SEQ ID NO: 6, (B) a protein comprising the amino acid sequence of the amino acid numbers 17 to 315 in SEQ ID NO: 6, (C) a protein comprising the amino acid sequence shown in SEQ ID NO: 6, but wherein one or several amino acid residues are substituted, deleted, inserted, added or inverted, and said protein has an L-lysine excretion activity, and (D) a protein comprising the amino acid sequence of the amino acid numbers 17 to 315 in SEQ ID NO: 6, but wherein one or several amino acid residues are substituted, deleted, inserted, added or inverted, and said protein has an L-lysine excretion activity.

It is a further aspect of the present invention to provide the method as described above, wherein the ybjE gene is a DNA selected from the group consisting of:

(A) a DNA comprising the nucleotide sequence shown in SEQ ID NO: 5, (B) a DNA comprising the nucleotide sequence of the nucleotide numbers 49 to 948 in SEQ ID NO: 5, (C) a DNA which is able to hybridize with a sequence complementary to the nucleotide sequence shown in SEQ ID NO: 5, or a probe which can be prepared from the nucleotide sequence under stringent conditions, and encodes a protein having an L-lysine excretion activity, and (D) a DNA which is able to hybridize with a sequence complementary to the nucleotide sequence of the nucleotide numbers 49 to 948 in SEQ ID NO: 5, or a probe which can be prepared from the nucleotide sequence under stringent conditions, and encodes a protein having an L-lysine excretion activity.

It is a further aspect of the present invention to provide the method as described above, wherein the L-amino acid is L-lysine, pH of the medium is controlled to be 6.0 to 9.0 during culture for the production, and 7.2 to 9.0 at the end of the culture, and there is a culture period where 20 mM or more of bicarbonate ions and/or carbonate ions are present in the medium so that the bicarbonate ions and/or carbonate ions act as counter ions of the basic amino acid.

It is a further aspect of the present invention to provide the method as described above, wherein the bacterium is an *Escherichia* bacterium.

It is a further aspect of the present invention to provide the method as described above, wherein the bacterium is *Escherichia coli*.

DETAILED DESCRIPTION OF EXEMPLARY EMBODIMENTS

Hereinafter, the present invention will be explained in detail.

<1> Bacterium

The bacterium in accordance with the presently disclosed subject matter is a bacterium which belongs to the family Enterobacteriaceae, has an L-amino acid-producing ability, and has been modified to increase expression of the gltP gene and/or the gltS gene. The L-amino acid can be L-lysine, L-threonine, L-aspartic acid, L-asparagine, L-methionine, L-alanine, L-isoleucine, or L-homoserine. If these L-amino acids are produced by fermentation using a microorganism, L-glutamic acid is often produced as a by-product. As is described herein, the production of the by-product L-glutamic acid can be reduced as compared to that observed in a non-modified strain by increasing expression of the gltP gene and/or the gltS gene in the bacterium. Such production can be reduced by 40% or more, 50% or more in another example, 60% or more in another example.

The L-amino acid-producing ability can mean the ability of the bacterium to produce an L-amino acid in a medium or the bacterial cells and cause accumulation of the L-amino acid to such an extent that the L-amino acid can be collected from the medium or the bacterial cells, when the bacterium is cultured in the medium. The bacterium may have the ability to produce L-lysine, L-threonine, L-aspartic acid, L-asparagine, L-methionine, L-alanine, L-isoleucine, and/or L-homoserine. The bacterium may inherently have the L-amino acid-producing ability, or may be modified to have an L-amino acid-producing ability by using a mutation method or DNA recombination techniques, as described herein.

The phrase "increase of expression of a gene" means to increase the transcription and/or translation of the gene.

<1-1> Impartation of L-Amino Acid-Producing Ability

Methods for imparting the ability to produce an L-amino acid such as L-lysine, L-threonine, L-aspartic acid, L-asparagine, L-methionine, L-isoleucine, L-alanine and L-homoserine to bacteria, and bacteria imparted with an ability to produce the L-amino acids described above are exemplified below. However, the bacterium is not limited to these examples, so long as a bacterium having an ability to produce an L-amino acid is used.

The bacterium is not particularly limited so long as the chosen bacterium belongs to the family Enterobacteriaceae, such as *Escherichia, Enterobacter, Pantoea, Klebsiella, Serratia, Erwinia, Salmonella* and *Morganella*, and having the aforementioned L-amino acid-producing ability. Specifically, those classified into the family Enterobacteriaceae according to the taxonomy used in the NCBI (National Center for Biotechnology Information) database (www.ncbi.nlm.nih.gov/Taxonomy/Browser/wwwtax.cgi?id=543) can be used. Examples of strains from the family Enterobacteriaceae which can be modified as described herein include a bacterium of the genus *Escherichia, Enterobacter,* or *Pantoea.*

Strains of *Escherichia* bacterium which can be modified to obtain *Escherichia* bacteria in accordance with the presently disclosed subject matter are not particularly limited, and specifically, those described in the work of Neidhardt et al. can be used (Backmann B. J., 1996, Derivations and Genotypes of some mutant derivatives of *Escherichia coli* K-12, p. 2460-2488, Table 1, In F. D. Neidhardt (ed.), *Escherichia coli* and *Salmonella* Cellular and Molecular Biology/Second Edition, American Society for Microbiology Press, Washington, D.C.). *Escherichia coli* is a particular example. Specific examples of *Escherichia coli* include *Escherichia coli* W3110 (ATCC 27325), *Escherichia coli* MG1655 (ATCC 47076), and so forth, which are derived from the prototype wild-type strain, K12 strain.

These strains are available from, for example, the American Type Culture Collection (P.O. Box 1549, Manassas, Va. 20108, United States of America). That is, registration numbers are given to each of the strains, and the strains can be ordered by using these registration numbers (refer to www.atcc.org/). The registration numbers of the strains are listed in the catalogue of the American Type Culture Collection.

Examples of the *Enterobacter* bacteria include *Enterobacter agglomerans*, *Enterobacter aerogenes* and so forth, and examples of the *Pantoea* bacteria include *Pantoea ananatis*. Some strains of *Enterobacter agglomerans* were recently reclassified into *Pantoea agglomerans*, *Pantoea ananatis*, or *Pantoea stewartii* on the basis of nucleotide sequence analysis of 16S rRNA etc. A bacterium belonging to any of the genus *Enterobacter* or *Pantoea* may be used so long as it is a bacterium classified into the family Enterobacteriaceae. When a *Pantoea ananatis* strain is bred by genetic engineering techniques, *Pantoea ananatis* AJ13355 strain (FERM BP-6614), AJ13356 strain (PERM BP-6615), AJ13601 strain (FERM BP-7207) and derivatives thereof can be used. These strains were identified as *Enterobacter agglomerans* when they were isolated, and deposited as *Enterobacter agglomerans*. However, they were recently re-classified as *Pantoea ananatis* on the basis of nucleotide sequencing of 16S rRNA and so forth as described above.

Methods for imparting the ability to produce an L-amino acid such as L-lysine, L-threonine, L-aspartic acid, L-asparagine, L-methionine, L-alanine, L-isoleucine and/or L-homoserine to bacteria belonging to the family Enterobacteriaceae, and methods for enhancing an ability to produce above-mentioned L-amino acids in bacteria belonging to the family Enterobacteriaceae are described below.

To impart the ability to produce an L-amino acid, methods conventionally employed in the breeding of coryneform bacteria or bacteria of the genus *Escherichia* can be used (see "Amino Acid Fermentation", Gakkai Shuppan Center (Ltd.), 1st Edition, published May 30, 1986, pp. 77-100). Such methods include by acquiring the properties of an auxotrophic mutant, an L-amino acid analogue-resistant strain, or a metabolic regulation mutant, or by constructing a recombinant strain so that it overexpresses an L-amino acid biosynthesis enzyme. Here, in the breeding of L-amino acid-producing bacteria, one or more of the above-described properties such as auxotrophy, analogue resistance, and metabolic regulation mutation can be imparted. The expression of L-amino acid biosynthesis enzyme(s) can be enhanced alone or in combinations of two or more. Furthermore, the methods of imparting properties such as an auxotrophy, analogue resistance, or metabolic regulation mutation can be combined with enhancement of the biosynthesis enzymes.

An auxotrophic mutant strain, L-amino acid analogue-resistant strain, or metabolic regulation mutant strain with the ability to produce an L-amino acid can be obtained by subjecting a parent or wild-type strain to conventional mutagenesis, such as exposure to X-rays or UV irradiation, or treatment with a mutagen such as N-methyl-N'-nitro-N-nitrosoguanidine (NTG) and ethyl methanesulfonate (EMS), then selecting those which exhibit autotrophy, analogue resistance, or a metabolic regulation mutation and which also have the ability to produce an L-amino acid from the obtained mutant strains.

L-Lysine-Producing Bacteria

L-Lysine-producing bacteria and methods for constructing them are exemplified below.

Examples of strains having L-lysine-producing ability include, for example, L-lysine analogue-resistant strains and metabolic regulation mutant strains. Examples of L-lysine analogues include, but are not limited to, oxalysine, lysine hydroxamate, S-(2-aminoethyl)-L-cysteine (AEC), γ-methyllysine, α-chlorocaprolactam, and so forth. Mutant strains having resistance to these lysine analogues can be obtained by subjecting a bacterium belonging to the family Enterobacteriaceae to a conventional artificial mutagenesis treatment. Specific examples of L-lysine-producing bacteria include *Escherichia coli* AJ11442 (FERM BP-1543, NRRL B-12185, see Japanese Patent Laid-open No. 56-18596 and U.S. Pat. No. 4,346,170), *Escherichia coli* VL611 strain (Japanese Patent Laid-open No. 2000-189180), and so forth. As an L-lysine-producing *Escherichia coli*, the WC196 strain may also be used (see International Patent Publication WO96/17930).

Furthermore, an L-lysine-producing bacterium can also be constructed by increasing activity of an L-lysine biosynthesis system enzyme. The activity of such an enzyme can be increased by increasing the copy number of the gene encoding the enzyme in the cells, or by modifying an expression control sequence thereof. Increasing the copy number of a gene encoding an enzyme of the L-lysine biosynthesis system and modifying an expression control sequence thereof can be attained by the same method as for the gltP and gltS genes described later.

Examples of genes encoding L-lysine biosynthetic enzymes include genes encoding enzymes of the diaminopimelate pathway such as dihydrodipicolinate synthase gene (dapA), aspartokinase gene (lysC), dihydrodipicolinate reductase gene (dapB), diaminopimelate decarboxylase gene (lysA), diaminopimelate dehydrogenase gene (ddh) (WO96/40934 for all the foregoing genes), phosphoenolpyruvate carboxylase gene (ppc) (Japanese Patent Laid-open No. 60-87788), aspartate aminotransferase gene (aspC) (Japanese Patent Publication (Kokoku) No. 6-102028), and aspartate semialdehyde dehydrogenase gene (asd) (WO00/61723), and genes encoding enzymes of the aminoadipic acid pathway such as homoaconitrate hydratase gene (Japanese Patent Laid-open No. 2000-157276). In addition, the bacterial strain may have an increased level of expression of the gene involved in energy efficiency (cyo) (European Patent Laid-open No. 1170376), the gene encoding nicotinamide nucleotide transhydrogenase (pntAB) (U.S. Pat. No. 5,830,716), the ybjE gene encoding a protein having L-lysine excretion activity (WO2005/073390), the gene encoding glutamate dehydrogenase (gdhA) (Gene 23:199-209, 1983), or any random combination of these. Abbreviations for the genes are shown in parentheses.

Among the aforementioned genes, the ybjE gene is preferred. Examples of the ybjE gene include the ybjE gene of *Escherichia coli* and homologues thereof. Examples of the ybjE gene of *Escherichia coli* include a gene encoding the amino acid sequence of amino acid numbers 17 to 315 in SEQ ID NO: 6, specifically a gene having the nucleotide sequence of nucleotide numbers 49 to 948 in SEQ ID NO: 5. In SEQ ID NO: 5, the start codon is estimated to be at nucleotide numbers 49 to 51. Although nucleotides 1 to 3 in SEQ ID NO: 5 constitute the codon encoding Val, that is, gtg, it may be translated as Met, or the start codon, and the protein encoded by the ybjE gene may be a protein having the amino acid sequence of SEQ ID NO: 6 (1 to 315). In this case, a DNA having the nucleotide sequence of nucleotide numbers 1 to 948 in SEQ ID NO: 5 can be used. However, it is clear from the examples that, regardless of which amino acid residue is the start codon, the microorganism for the production method as described in the presently disclosed subject matter can be obtained by using a DNA containing the nucleotide sequence of nucleotide numbers 49 to 948 in SEQ ID NO: 1.

It is known that the wild-type dihydrodipicolinate synthase derived from *Escherichia coli* is subject to feedback inhibition by L-lysine, and it is known that the wild-type aspartokinase derived from *Escherichia coli* is subject to suppression and feedback inhibition by L-lysine. Therefore, when the dapA gene and lysC gene are used, genes encoding mutant enzymes desensitized to the feedback inhibition by L-lysine can be used.

Examples of DNA encoding a mutant dihydrodipicolinate synthetase desensitized to feedback inhibition by L-lysine include a DNA encoding such a protein having an amino acid sequence in which the histidine residue at the position 118 is replaced by tyrosine residue. Examples of DNA encoding a mutant aspartokinase desensitized to feedback inhibition by L-lysine include a DNA encoding an AKIII protein having an amino acid sequence in which the threonine residue at the position 352, the glycine residue at the position 323, and the methionine residue at the position 318 are replaced by isoleucine, asparagine, and isoleucine residues, respectively (for these mutants, see U.S. Pat. Nos. 5,661,012 and 6,040,160). Such mutant DNAs can be obtained by site-specific mutagenesis using PCR or the like.

Wide host-range plasmids RSFD80, pCAB1, and pCABD2 are known to contain a mutant dapA gene encoding a mutant dihydrodipicolinate synthase and a mutant lysC gene encoding a mutant aspartokinase (U.S. Pat. No. 6,040, 160). *Escherichia coli* JM109 strain transformed with this plasmid was named AJ12396 (U.S. Pat. No. 6,040,160), and the strain was deposited at the National Institute of Bioscience and Human-Technology, Agency of Industrial Science and Technology, Ministry of International Trade and Industry (currently National Institute of Advanced Industrial Science and Technology, International Patent Organism Depositary) on Oct. 28, 1993 and assigned an accession number of FERM P-13936, and the deposit was then converted to an international deposit under the provisions of Budapest Treaty on Nov. 1, 1994 and assigned an accession number of FERM BP-4859. RSFD80 can be obtained from the AJ12396 strain by a conventional method.

Furthermore, L-amino acid-producing bacteria may have reduced or no activity of an enzyme that catalyzes a reaction which causes a branching off from the L-amino acid biosynthesis pathway and results in the production of another compound. Also, the bacteria may have reduced or no activity of an enzyme that negatively acts on L-amino acid synthesis or accumulation. Examples of such enzymes involved in L-lysine production include homoserine dehydrogenase, lysine decarboxylase (cadA, ldcC), malic enzyme, and so forth, and strains in which activities of these enzymes are decreased or deleted are disclosed in WO95/23864, WO96/17930, WO2005/010175, and so forth.

Expression of both the cadA and ldcC genes encoding lysine decarboxylase can be decreased in order to decrease or delete the lysine decarboxylase activity. Expression of the both genes can be decreased by, for example, the method described in WO2006/078039.

In order to reduce or eliminate activities of these enzymes, a mutation may be introduced into the genes encoding the enzymes on the genome by a known mutagenesis method or gene recombination technique so that intracellular activities of the enzymes are reduced or eliminated. Such introduction of a mutation can be achieved by, for example, using genetic recombination to eliminate the genes encoding the enzymes on the genome or to modify an expression control sequence such as a promoter or the Shine-Dalgarno (SD) sequence. A mutation can also be introduced to impart an amino acid substitution (missense mutation), a stop codon (nonsense mutation), or a frame shift mutation which results in the addition or deletion of one or two nucleotides into the regions encoding the enzymes on the genome, or partially or totally deleting the genes (J. Biol. Chem., 272:8611-8617, 1997). The enzymatic activities can also be decreased or eliminated by constructing a gene encoding a mutant enzyme, in which the coding region is entirely or partially deleted, and substituting it for a normal gene on the genome by homologous recombination or the like, or by introducing a transposon or IS factor into the gene.

For example, in order to introduce a mutation that decreases or eliminates the activities of the above-mentioned enzymes by genetic recombination, the following methods can be used. A mutant gene is prepared by modifying part of the sequence of an objective gene so that it does not encode an enzyme that can function normally, and then a bacterium belonging to the family Enterobacteriaceae can be transformed with a DNA containing the mutant gene to cause recombination of a corresponding gene on the genome with the mutant gene to substitute the mutant gene for the objective gene on the genome. Examples of such gene substitution using homologous recombination include methods of using a linear DNA such as the method called Red-driven integration (Datsenko, K. A, and Wanner, B. L., 2000, Proc. Natl. Acad. Sci. USA, 97:6640-6645), and the method utilizing the Red driven integration in combination with an excisive system derived from 2, phage (Cho, E. H., Gumport, R. I., Gardner, J. F., 2002, J. Bacteriol., 184:5200-5203) (refer to WO2005/010175), a method of using a plasmid containing a temperature sensitive replication origin (U.S. Pat. No. 6,303,383, Japanese Patent Laid-open No. 05-007491), and so forth. Furthermore, such site-specific mutagenesis based on gene substitution using homologous recombination as described above can also be performed by using a plasmid that is unable to replicate in a host.

Examples of L-lysine-producing bacteria include *Escherichia coli* WC196ΔcadAΔldcC/pCABD2 (WO2006/078039). The strain was constructed by introducing the plasmid pCABD2 containing lysine biosynthesis genes (U.S. Pat. No. 6,040,160) into the WC196 strain having disrupted cadA and ldcC genes, which encode lysine decarboxylase. The WC196 strain was bred from the W3110 strain, which was derived from *Escherichia coli* K-12, by replacing the wild-type lysC gene on the chromosome of the W3110 strain with a mutant lysC gene encoding a mutant aspartokinase III in which threonine at position 352 was replaced with isoleucine, resulting in desensitization of the feedback inhibition thereof by L-lysine (U.S. Pat. No. 5,661,012), and conferring AEC resistance to the resulting strain (U.S. Pat. No. 5,827,698). The WC196 strain was designated *Escherichia coli* AJ13069, deposited at the National Institute of Bioscience and Human-Technology, Agency of Industrial Science and Technology (currently the independent administrative agency, National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994, and assigned an accession number of FERM P-14690. Then, it was converted to an international deposit under the provisions of the Budapest Treaty on Sep. 29, 1995, and assigned an accession number of FERM BP-5252 (U.S. Pat. No. 5,827,698). The WC196ΔcadAΔldcC strain itself is also an exemplary L-lysine-producing bacterium. The WC196ΔcadAΔldcC was designated AJ110692, and deposited at the National Institute of Bioscience and Human-Technology, Agency of Industrial Science and Technology (currently the independent administrative agency, National Institute of Advanced Industrial Science and Technology, International Patent Organism Depositary (Tsukuba Central 6, 1-1, Higashi 1-Chome, Tsukuba-shi, Ibaraki-ken, 305-8566, Japan) on Oct. 7, 2008 as an international deposit and assigned an accession number of FERM BP-11027.

The plasmid pCABD2 contains a mutant dapA gene derived from *Escherichia coli* that encodes a dihydrodipicolinate synthase (DDPS) having a mutation for desensitization to the feedback inhibition by L-lysine, a mutant lysC gene derived from *Escherichia coli* that encodes aspartokinase III having a mutation for desensitization to the feedback inhibition by L-lysine, the dapB gene derived from *Escherichia coli* that encodes dihydrodipicolinate reductase, and the ddh gene derived from *Brevibacterium lactofermentum* that encodes diaminopimelate dehydrogenase.

L-Threonine-Producing Bacteria

Examples of L-threonine-producing bacteria include bacteria belonging to the family Enterobacteriaceae in which one or more activities of the L-threonine biosynthesis system enzymes are enhanced. Examples of genes encoding L-threonine biosynthetic enzymes include aspartokinase III gene (lysC), aspartate semialdehyde dehydrogenase gene (asd), aspartokinase I gene (thrA), homoserine kinase gene (thrB), and threonine synthase gene (thrC) encoded by the thr operon. Two or more of these genes may be introduced. The genes encoding the L-threonine biosynthetic enzymes may be introduced into an Enterobacteriaceae bacterium in which the decomposition of threonine is decreased. Examples of such *Escherichia* bacterium include, for example, the TDH6 strain which is deficient in threonine dehydrogenase activity (Japanese Patent Laid-open No. 2001-346578), and so forth.

The enzymatic activities of the L-threonine biosynthetic enzymes are inhibited by the end product, L-threonine. Therefore, for constructing L-threonine-producing strains, the genes for the L-threonine biosynthetic enzymes can be modified so that the enzymes are desensitized to feedback inhibition by L-threonine in the L-threonine-producing strains. The aforementioned thrA, thrB, and thrC genes constitute the threonine operon, which forms an attenuator structure. The expression of the threonine operon is inhibited by isoleucine and threonine in the culture medium and also suppressed by attenuation. Therefore, the threonine operon can be modified by removing the leader sequence in the attenuation region or the attenuator (refer to Lynn, S. P., Burton, W. S., Donohue, T. J., Gould, R. M., Gumport, R. L, and Gardner, J. F., J. Mol. Biol. 194:59-69 (1987); WO02/26993; WO2005/049808).

The native promoter of the threonine operon is present upstream of the threonine operon, and can be replaced with a non-native promoter (refer to WO98/04715), or a threonine operon which has been modified so that expression of the threonine biosynthesis gene is controlled by the repressor and promoter of 2-phage can be constructed (refer to European Patent No. 0593792). Furthermore, in order to modify an *Escherichia* bacterium so that it is desensitized to feedback inhibition by L-threonine, a strain resistant to α-amino-β-hydroxyisovaleric acid (AHV) can be selected.

The copy number of the threonine operon that is modified to desensitize to feedback inhibition by L-threonine can be increased, or the expression of the threonine operon can be increased by ligating it to a potent promoter. The copy number can also be increased by, besides amplification using a plasmid, transferring the threonine operon to a genome using a transposon, Mu-phage, or the like.

As the aspartokinase III gene (lysC), a gene modified so that the enzyme is desensitized to feedback inhibition by L-lysine can be used. Such a lysC gene modified so that the enzyme is desensitized to the feedback inhibition can be obtained by the method described in U.S. Pat. No. 5,932,453.

Other than increasing expression of the L-threonine biosynthetic genes, expression of the genes involved in the glycolytic pathway, TCA cycle, or respiratory chain, the genes that regulate the expression of these genes, or the genes involved in sugar uptake can also be increased. Examples of such genes effective for L-threonine production include the genes encoding transhydrogenase (pntAB, European Patent No. 733712), phosphoenolpyruvate carboxylase (pepC, WO95/06114), phosphoenolpyruvate synthase (pps, European Patent No. 877090), and a gene encoding pyruvate carboxylase from coryneform bacterium or *Bacillus* bacterium (WO99/18228, European Patent Laid-open No. 1092776).

L-Threonine-producing bacteria can also be obtained by enhancing expression of a gene that imparts L-threonine resistance and/or a gene that imparts L-homoserine resistance, or by imparting L-threonine resistance and/or L-homoserine resistance to the host bacterium. Examples of the genes that impart the above-mentioned resistance include the rhtA gene (Res. Microbiol. 154:123-135 (2003)), rhtB gene (European Patent Laid-open No. 0994190), rhtC gene (European Patent Laid-open No. 1013765), yfiK gene, and yeaS gene (European Patent Laid-open No. 1016710). Exemplary methods for imparting L-threonine resistance to a host bacterium include those described in European Patent Laid-open No. 0994190 or WO90/04636.

*E. coli* VKPM B-3996 (U.S. Pat. No. 5,175,107) can be exemplified as an L-threonine-producing bacterium. The strain VKPM B-3996 was deposited on Apr. 7, 1987 at the Russian National Collection of Industrial Microorganisms (VKPM), GNII Genetika (Russia, 117545 Moscow 1, Dorozhny proezd, 1) under the registration number VKPM B-3996. The VKPM B-3996 strain contains the plasmid pVIC40 (WO90/04636), which was obtained by inserting the threonine biosynthetic genes (threonine operon, thrABC) into a wide host range plasmid vector pAYC32 containing the streptomycin resistance marker (Chistorerdov, A. Y., and Tsygankov, Y. D., Plasmid, 16, 161-167 (1986)). In pVIC40, aspartokinase I-homoserine dehydrogenase I encoded by the thrA gene in the threonine operon is desensitized to feedback inhibition by L-threonine.

*E. coli* VKPM B-5318 (refer to European Patent No. 0593792) is also an example of an L-threonine-producing bacterium. The VKPM B-5318 strain was deposited in the Russian National Collection of Industrial Microorganisms (VKPM) GNII Genetika on May 3, 1990 under a registration number of VKPM B-5318. The VKPM B-5318 strain is prototrophic with regard to L-isoleucine, and harbors a recombinant plasmid DNA constructed so that the threonine operon, that is, the threonine biosynthesis genes, is deficient in the attenuator region. This attenuator region is native to the strain, and is located downstream from the λ phage-derived temperature-sensitive C1 repressor, PR-promoter, and the gene encoding N-terminal of Cro protein. Therefore, the expression of the threonine biosynthesis genes is regulated by the repressor and the promoter derived from λ phage.

L-Homoserine-Producing Bacteria

Examples of L-homoserine-producing bacteria belonging to the genus *Escherichia* include the NZ10(thrB) strain, which is a Leu+ revertant derived from the known strain C600 (thrB, leuB, refer to Appleyard R. K., Genetics, 39, 440-452, 1954). A NZ10 transformant strain transformed with the thrA gene encoding aspartokinase-homoserine dehydrogenase I can also be used.

If the copy number of the rhtB gene of a bacterium is increased, the bacterium becomes resistant to L-homoserine, and productivity thereof for L-homoserine, L-threonine, L-alanine, L-valine and L-isoleucine is improved (European Patent Laid-open No. 994190 A2). Furthermore, if the copy number of the rthC gene of a bacterium is increased, the bacterium becomes resistant to L-homoserine and L-threonine, and the productivity thereof for L-homoserine, L-threonine and L-leucine is improved (European Patent Laid-open No. 1013765 A1).

Furthermore, the *Escherichia coli* 44 strain (deposited at the Russian National Collection of Industrial Microorganisms with a registration number of VKPM B-2175) can also be used.

L-Methionine-Producing Bacteria

Examples of L-methionine-producing bacteria belonging to the genus *Escherichia* include such strains as *Escherichia coli* AJ11539 (NRRL B-12399), AJ11540 (NRRL B-12400), AJ11541 (NRRL B-12401), AJ11542 (NRRL B-12402, GB 2075055), 218 (VKPM B-8125, European Patent No. 1239041), and so forth.

L-Aspartic Acid-Producing Bacteria

Examples of L-aspartic acid-producing bacteria belonging to the genus *Escherichia* include the *Escherichia coli* strain in which aspartase activity resulting in generating L-aspartic acid from fumaric acid is enhanced (Japanese Patent Publication No. 38-6588).

L-Alanine-Producing Bacteria

L-Alanine is produced by β-decarboxylation of aspartic acid. Therefore, examples of L-alanine-producing bacteria belonging to the genus *Escherichia* include the *Escherichia coli* strain in which aspartate β-decarboxylase is enhanced (Japanese Patent Laid-open No. 2-242690).

L-Isoleucine-Producing Bacteria

Examples of parent strains which can be used to derive L-isoleucine-producing bacteria include, but are not limited to, mutants which are resistant to 6-dimethylaminopurine (Japanese Patent Laid-open No. 5-304969), mutants which are resistant to isoleucine analogues such as thiaisoleucine and isoleucine hydroxamate, and mutants which are additionally resistant to DL-ethionine and/or arginine hydroxamate (Japanese Patent Laid-open No. 5-130882). In addition, recombinant strains transformed with genes encoding proteins involved in L-isoleucine biosynthesis, such as threonine deaminase and acetohydroxate synthase, are also used as parent strains (Japanese Patent Laid-open No. 2-458, FR 0356739, and U.S. Pat. No. 5,998,178).

L-Asparagine-Producing Bacteria

L-Asparagine is produced by transferring an amino group to aspartic acid (Boehlein, S. K., Richards, N. G. J., & Schuster, S. M. (1994a), J. Biol. Chem., 269, 7450-7457). Therefore, examples of L-asparagine-producing bacteria belonging to the genus *Escherichia* include L-aspartic acid-producing *Escherichia coli* strains in which asparagine synthetase is enhanced.

The bacterium can be obtained by modifying such a bacterium having an ability to produce an L-amino acid selected from L-lysine, L-threonine, L-aspartic acid, L-asparagine, L-methionine, L-alanine, L-isoleucine and L-homoserine as described above so that expression of the gltP gene and/or the gltS gene thereof is increased. Alternatively, the bacterium can also be obtained by imparting an ability to produce such an L-amino acid to a bacterium which has been modified so that expression of the gltP gene and/or the gltS gene thereof is increased.

The phrase "being modified so that expression of the gltP gene and/or the gltS gene thereof is increased" can mean that the number of the molecules encoded by the gltP gene and/or the gltS gene per cell increases, or the activity of the GltP protein or the GltS protein encoded by these genes per molecule improves, as compared to an unmodified strain such as a wild-type or parent strain. The bacterium can be modified so that the activity of the GltP protein or the GltS protein per cell increases to 150% or more, 200% or more in another example, 300% or more in another example, of the activity of an unmodified strain. Examples of an unmodified strain serving as a reference for the above comparison such as a wild-type strain of a microorganism belonging to the family Enterobacteriaceae include, for example, the *Escherichia coli* MG1655 strain (ATCC 47076), W3110 strain (ATCC 27325), *Pantoea ananatis* AJ13335 strain (FERM BP-6614), and so forth. The activities of the GltP and the GltS proteins refer to activities responsible for uptake of L-glutamic acid into bacterial cells from the outside of the cells, and are referred to as "L-glutamate transporter activity". The L-glutamate transporter activity can be confirmed by comparing the velocity of uptake of L-glutamate into cells of the microorganism with L-glutamate uptake velocity of a corresponding unmodified strain. The velocity of uptake of L-glutamate can be measured by, for example, reacting live cells with L-glutamic acid labeled with RI for a certain period of time, and detecting radioactivity in the cells (Wallace, B; Yang, Y J; Hong, J S; Lum, D, J. Bacteriol., 1990 June; 172(6):3214-3220).

An increase of expression of the gltP gene and/or the gltS gene as compared to that of an unmodified strain such as a parent or wild-type strain can be confirmed by comparing the amount of mRNA of the gene with that of the wild-type or unmodified strain. Examples of the method for confirming the expression amount include Northern hybridization and reverse transcriptase PCR (RT-PCR, Molecular Cloning, Cold Spring Harbor Laboratory Press, Cold Spring Harbor, USA, 2001). The expression may be increased to any level so long as the level is increased as compared to that of an unmodified strain, and for example, it can be increased not less than 1.5 times, not less than 2 times in another example, not less than 3 times in another example, as compared to that of, for example, an unmodified strain. Furthermore, enhancement of the activities of the proteins encoded by the gltP gene and/or the gltS gene can also be confirmed on the basis of an increase in the amount of the target protein as compared to that in an unmodified strain, and it can be detected by, for example, Western blotting using an antibody (Molecular Cloning, Cold Spring Harbor Laboratory Press, Cold Spring Harbor, USA, 2001).

The gltP and gltS genes can refer to the gltP and gltS genes from, or native to, a microorganism belonging to the family Enterobacteriaceae, or homologues thereof. As the gltP gene of *Escherichia coli*, a gene encoding a protein having the amino acid sequence of SEQ ID NO: 2 (SEQ ID NO: 1) can be exemplified (b4077, GenBank Accession No. NP_418501. [gi:16131903]). As the gltS gene from, or native to, *Escherichia coli*, a gene encoding a protein having the amino acid sequence of SEQ ID NO: 4 (SEQ ID NO: 3) can be exemplified (b3653, GenBank Accession No. NP_418110. [gi:16131524]).

A homologue of the gltP or gltS gene can refer to a gene derived from another microorganism, but showing high structural similarity to the gltP gene or the gltS gene of an *Escherichia* bacterium and encoding a protein having the activity of reducing the by-production of L-glutamic acid when producing an L-amino acid such as L-lysine, L-threonine, L-aspartic acid, L-asparagine, L-methionine, L-alanine, L-isoleucine, and/or L-homoserine, and the activity of taking up glutamic acid into the cells, when the gene is introduced into a host. Examples of a gltP or gltS gene homologue include, for example, homologous genes registered at GenBank, including those derived from, or native to, *Shigella* and *Enterobacter* bacteria. Furthermore, the gltP gene and/or the gltS gene may be cloned from a *Streptomyces* bacterium such as *Streptomyces coelicolor* or a lactic acid bacterium of the genus *Lactococcus, Lactobacillus* or the like on the basis of homology to the genes exemplified above. Any gene having high homology to the gltP gene and/or the gltS gene from *Escherichia* bacterium may be used, even though the gene may have a different name. The gltP gene and/or gltS gene homologues include, for example, genes that can be cloned by using the synthetic oligonucleotides of SEQ ID NOS: 8 and 9, or SEQ ID NOS: 10 and 11.

Furthermore, a gltP and/or gltS gene homologue having high homology can be obtained from a known database on the basis of the aforementioned sequence information. Homology of amino acid sequences and nucleotide sequences can be determined by using, for example, the algorithm BLAST of Karlin and Altschul (Proc. Natl. Acad. Sci. USA, 90, 5873 (1993)) or FASTA (Methods Enzymol., 183, 63 (1990)). Programs called BLASTN and BLASTX have been developed on the basis of this algorithm BLAST (refer to www.ncbi.nlm.nih.gov).

The term "homology" may also refer to "identity".

Homologues which are highly homologous to the gltP or gltS gene from, or native to, *Escherichia coli* are described below with homologies, names of bacteria, and registration numbers in gene sequence databases.

TABLE 1

| Identity | Source | Acc. No. |
| --- | --- | --- |
| 100% | *Escherichia coli* (strain K12) | EMBL; M32488; AAA23832.1 |
| 99% | *Escherichia coli* | CP000247 |
| 99% | *Shigella boydii* (Sb227) | CP000034-CP000039 |
| 99% | *Shigella sonnei* (Ss046) | CP000034-CP000039 |
| 99% | *Escherichia coli* O157:H7 | EMBL; AE005174; AAG59275.1 |
| 99% | *Escherichia coli* O6 | EMBL; AE014075; AAN83500.1 |
| 99% | *Shigella sonnei* (strain Ss046) | EMBL; CP000038; AAZ90754.1 |
| 99% | *Shigella boydii* serotype 4 (strain Sb227) | EMBL; CP000036; ABB68540.1 |
| 99% | *Escherichia coli* O6:K15:H31 (strain 536/UPEC) | EMBL; CP000247; ABG72258.1 |
| 99% | *Shigella boydii* serotype 18 (strain CDC 3083-94/BS512) | EMBL; CP001063; ACD08193.1 |
| 99% | *Escherichia coli* O157:H7 str. EC4076 | EMBL; ABHQ01000005; EDU70808.1 |
| 99% | *Escherichia coli* O157:H7 str. EC4113 | EMBL; ABHP01000005; EDU55567.1 |
| 99% | *Escherichia coli* O157:H7 str. EC4196 | EMBL; ABHO01000008; EDU33758.1 |
| 99% | *Escherichia coli* (strain SMS-3-5/SECEC) | EMBL; CP000970; ACB19931.1 |
| 99% | *Escherichia coli* (strain ATCC 8739/DSM 1576/Crooks) | EMBL; CP000946; ACA79551.1 |
| 99% | *Escherichia coli* (UTI89) | EMBL; CP000243/CP000244 |
| 99% | *Escherichia coli* O1:K1/APEC | EMBL; CP000468; ABJ03557.1 |
| 99% | *Escherichia coli* (strain UTI89/UPEC) | EMBL; CP000243; ABE10076.1 |
| 99% | *Escherichia coli* 53638 | EMBL; AAKB02000001; EDU65993.1 |
| 99% | *Escherichia coli* O9:H4 (strain HS) | EMBL; CP000802; ABV08482.1 |
| 99% | *Escherichia coli* O139:H28 (strain E24377A/ETEC) | EMBL; CP000800; ABV17642.1 |
| 99% | *Shigella flexneri* | EMBL; AE005674; AAN45560.1 |
| 99% | *Shigella flexneri* serotype 5b (strain 8401) | EMBL; CP000266; BF06119.1 |
| 98% | *Escherichia albertii* TW07627 | EMBL; ABKX01000015; EDS90170.1 |
| 95% | *Citrobacter koseri* (strain ATCC BAA-895/CDC 4225-83/SGSC4696) | EMBL; CP000822; ABV14881.1 |
| 94% | *Salmonella paratyphi* B (strain ATCC BAA-1250/SPB7) | EMBL; CP000886; ABX70555.1 |
| 94% | *Salmonella typhimurium* | EMBL; AE008901; AAL23107.1 |
| 94% | *Salmonella paratyphi* A | EMBL; CP000026; AAV79845.1 |
| 93% | *Salmonella arizonae* (strain ATCC BAA-731/CDC346-86/RSK2980) | EMBL; CP000880; ABX23224.1 |
| 93% | *Salmonella typhi* | EMBL; AE014613; AAO71654.1 |
| 93% | *Enterobacter* sp. (strain 638) | EMBL; CP000653; ABP58966.1 |
| 93% | *Salmonella choleraesuis* | EMBL; AE017220; AAX68069.1 |
| 93% | *Klebsiella pneumoniae* subsp. *pneumoniae* (strain ATCC 700721/MGH78578) | EMBL; CP000647; ABR79835.1 |

TABLE 1-continued

| Identity | Source | Acc. No. |
| --- | --- | --- |
| 90% | Enterobacter sakazakii (strain ATCC BAA-894) | EMBL; CP000783; ABU75428.1 |

TABLE 2

| Identity | Source | Acc. No. |
| --- | --- | --- |
| 100% | Escherichia coli | |
| 99% | Escherichia coli O157:H7 | EMBL; BA000007; BAB37952.1 |
| 99% | Escherichia coli O157:H7 str. EC4076 | EMBL; ABHQ1000003; EDU71328.1 |
| 99% | Escherichia coli O157:H7 str. EC4113 | EMBL; ABHP01000008; EDU54990.1 |
| 99% | Escherichia coli O157:H7 str. EC4196 | EMBL; ABHO01000001; EDU35455.1 |
| 99% | Escherichia coli O9:H4 (strain HS) | EMBL; CP000802; ABV08069.1 |
| 99% | Escherichia coli O139:H28 (strain E24377A/ ETEC) | EMBL; CP000800; ABV17638.1 |
| 99% | Escherichia coli (strain SMS-3-5/ SECEC) | EMBL; CP000970; ACB18417.1 |
| 99% | Escherichia coli 53638 | EMBL; AAKB02000001; EDU64770.1 |
| 99% | Escherichia coli | D00626 |
| 99% | Escherichia coli UTI89 | Acc. No. CP000243/ CP000244 |
| 99% | Escherichia coli O1:K1/APEC | EMBL; CP000468; ABJ03124.1 |
| 99% | Escherichia coli (strain UTI89/ UPEC) | EMBL; CP000243; ABE09626.1 |
| 99% | Escherichia albertii TW07627 | EMBL; ABKX01000002; EDS93075.1 |
| 98% | Escherichia coli 536 | CP000247 |
| 98% | Escherichia coli O6 | EMBL; AE014075; AAN82914.1 |
| 98% | Escherichia coli O6:K15:H31 (strain 536/UPEC) | EMBL; CP000247; ABG71723.1 |
| 99% | Escherichia coli O157:H7 | EMBL; AE005174; AAG58798.1 |
| 93% | Salmonella choleraesuis | EMBL; AE017220; AAX67576.1 |
| 93% | Salmonella paratyphi A | EMBL; CP000026; AAV79398.1 |
| 93% | Salmonella paratyphi B (strain ATCC BAA-1250/ SPB7) | EMBL; CP000886; ABX69959.1 |
| 92% | Salmonella typhimurium | EMBL; AE008874; AAL22605.1 |
| 93% | Salmonella arizonae (strain ATCC BAA-731/ CDC346-86/ RSK2980) | EMBL; CP000880; ABX23688.1 |
| 93% | Salmonella typhi | EMBL; AE014613; AAO71256.1 |
| 92% | Salmonella typhi | EMBL; AL627280; CAD03248.1 |

The consensus amino acid sequence based on the aforementioned homologues is shown in SEQ ID NO: 12 for GltP and SEQ ID NO: 13 for GltS.

Furthermore, the gltP and the gltS genes are not limited to their respective wild-type genes, but they can also be mutant or artificially modified genes encoding proteins having the amino acid sequence of SEQ ID NOs: 2, 4, 12 or 13, but which include substitutions, deletions, insertions, additions or the like of one or more amino acid residues at one or more positions so long as the function of the encoded protein, that is, the L-glutamate transporter activity, is not degraded.

Although the number meant by the phrase "one or several" may differ depending on the position in the three-dimensional structure of the protein or the types of amino acid residues, specifically, it can be 1 to 20, 1 to 10 in another example, 1 to 5 in another example. The aforementioned substitutions, deletions, insertions or additions of one or more amino acid residues can be a conservative mutation that maintains the L-glutamate transporter activity. The conservative mutation can typically be a conservative substitution. The conservative substitution can be a substitution wherein substitution takes place mutually among Phe, Trp and Tyr, if the substitution site is an aromatic amino acid; among Leu, Ile and Val, if the substitution site is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having hydroxyl group. Specific examples of substitutions which are considered conservative substitutions include substitution of Ser or Thr for Ala; substitution of Gln, His or Lys for Arg; substitution of Glu, Gln, Lys, His or Asp for Asn; substitution of Asn, Glu or Gln for Asp; substitution of Ser or Ala for Cys; substitution of Asn, Glu, Lys, His, Asp or Arg for Gln; substitution of Gly, Asn, Gln, Lys or Asp for Glu; substitution of Pro for Gly; substitution of Asn, Lys, Gln, Arg or Tyr for His; substitution of Leu, Met, Val or Phe for Ile; substitution of Ile, Met, Val or Phe for Leu; substitution of Asn, Glu, Gln, His or Arg for Lys; substitution of Ile, Leu, Val or Phe for Met; substitution of Trp, Tyr, Met, Ile or Leu for Phe; substitution of Thr or Ala for Ser; substitution of Ser or Ala for Thr; substitution of Phe or Tyr for Trp; substitution of His, Phe or Trp for Tyr; and substitution of Met, Ile or Leu for Val. The mutation of such substitution, deletion, insertion, addition, inversion or the like of amino acid residues as described above can also include a naturally occurring mutation based on individual differences, differences in species of microorganisms having the gltP gene and/or the gltS gene (mutant or variant) and so forth. A gene having such a mutation can be obtained by modifying the nucleotide sequence of SEQ ID NO: 1 or 3 or a homologue thereof by, for example, site-specific mutagenesis, so that substitution, deletion, insertion or addition of an amino acid residue or residues is included in the encoded protein at a specific site.

Furthermore, as the gltP gene and/or the gltS gene, a gene encoding a protein having a homology of 80% or more, 90% or more in another example, 95% or more in another example, 97% or more in another example, to the entire amino acid sequence of SEQ ID NO: 2, 4, 12 or 13, and having the L-glutamate transporter activity may be used.

Furthermore, codons of the gltP gene and/or the gltS gene may be replaced with those easily used by the chosen host into which the gltP gene and/or the gltS gene is/are introduced. Moreover, so long as the L-glutamate transporter activity is maintained, the protein encoded by the gltP gene or the gltS gene may be a protein in which N- or C-terminus sequence is elongated or deleted. The length of amino acid sequence to be elongated or deleted can be 50 or less, 20 or less in another example, 10 or less in another example, 5 or less in another example, in terms of number of amino acid residues. More specifically, the protein may be a protein having the amino acid sequence of SEQ ID NO: 2, but with elongation or deletion of 5 to 50 amino acid residues on the N-terminal side or 5 to 50 amino acid residues on the C-terminal side.

Moreover, a modified gltP gene and/or gltS gene can also be obtained by conventionally known mutation treatments as described below. Examples of the mutation treatment include treating one or more of the gltP gene and/or the gltS gene with hydroxylamine or the like in vitro, and treating a microorganism, for example, *Escherichia* bacteria, containing the gene with ultraviolet ray irradiation or a known mutagen such as N-methyl-N'-nitro-N-nitrosoguanidine (NTG) or ethyl methanesulfonate (EMS). Whether such a modified gene encodes a protein having the L-glutamate transporter activity can be confirmed by, for example, allowing expression of the gene in an appropriate cell, and examining whether the protein has the L-glutamate transporter activity.

Moreover, the gltP gene and/or the gltS gene may also be a DNA which is hybridizable with a sequence which is complementary to the nucleotide sequence of SEQ ID NO: 1 or 3, respectively, or a probe that can be prepared from such sequences, under stringent conditions, and encoding a protein having the L-glutamate transporter activity. The "stringent conditions" can mean conditions under which specific hybrids are formed, but non-specific hybrids are not formed. Although it is difficult to definitely define the conditions numerically, examples include, conditions under which DNAs that are highly homologous to each other, for example, DNAs having a homology of not less than 80%, not less than 90% in another example, not less than 95% in another example, not less than 97% in another example, hybridize with each other, and DNAs having a homology lower than the above levels do not hybridize with each other. Such conditions also include washing in accordance with typical Southern hybridization, that is, washing once, twice or three times, at salt concentrations and temperature of 1×SSC, 0.1% SDS at 60° C., 0.1×SSC, 0.1% SDS at 60° C. in another example, 0.1×SSC, 0.1% SDS at 68° C. in another example.

As the probe, a part of the complementary sequence of the sequence of SEQ ID NO: 1 may also be used. Such a probe can be produced by PCR using oligonucleotides prepared on the basis of the complementary sequence of SEQ ID NO: 1 as primers, and a DNA fragment containing the nucleotide sequence as a template. For example, when a DNA fragment having a length of about 300 bp is used as the probe, the washing conditions after hybridization can be exemplified by 2×SSC, 0.1% SDS at 50° C.

To enhance expression of the gltP and/or the gltS gene, the copy number of the gene can be increased in cells utilizing, for example, gene recombination techniques. For example, the copy number of the gene can be increased by ligating a DNA fragment containing the gltP gene and/or the gltS gene to a vector which functions in the host bacterium, such as a multi copy vector, to prepare a recombinant DNA, and introducing it into the bacterium to transform the bacterium.

When the gltP gene of *Escherichia coli* is used, it can be obtained by PCR (polymerase chain reaction, refer to White, T. J. et al., Trends Genet., 5, 185 (1989)) using primers prepared on the basis of the nucleotide sequence of SEQ ID NO: 1, for example, the primers shown in SEQ ID NOS: 8 and 9, and a genomic DNA of *Escherichia coli* as a template. The gltP genes derived from other bacteria belonging to the family Enterobacteriaceae can also be obtained from the genomic DNA of the respective microorganism, or a genomic DNA library by PCR using, as primers, oligonucleotides prepared based on the gltP gene known for the bacterium or a bacterium of another species, or amino acid sequence information of the protein encoded by the gltP gene, or hybridization using an oligonucleotide prepared based on such sequence information as described above as a probe. A genomic DNA can be prepared from a microorganism that serves as a DNA donor by, for example, the method of Saito and Miura (Saito H. and Miura K., Biochem. Biophys. Acta, 72, 619, 1963; Experiment Manual for Biotechnology, edited by The Society for Biotechnology, Japan, pp. 97-98, Baifukan Co., Ltd., 1992) or the like.

Then, the gltP gene and/or the gltS gene amplified by PCR can be ligated to a vector DNA that can function in cells of the chosen host bacterium to prepare a recombinant DNA. Examples of the vector which can function in cells of a host bacterium include vectors autonomously replicable in cells of the host bacterium. Examples of autonomously replicable vectors in *Escherichia coli* cells include pUC19, pUC18, pHSG299, pHSG399, pHSG398, pACYC184, (pHSG and pACYC series vectors are available from Takara Bio Inc.), RSF1010, pBR322, pMW219 (pMW219 is available form Nippon Gene Co., Ltd.), pSTV29 (available form Takara Bio Inc.), and so forth.

In order to introduce a recombinant DNA prepared as described above into a bacterium, any known transformation method reported so far can be employed. For example, there are a methods of treating recipient cells with calcium chloride so as to increase permeability for DNA, which has been reported for *Escherichia coli* K-12 (Mandel, M. and Higa, A., J. Mol. Biol., 53, 159 (1970)), and a method of using competent cells prepared from growing cells and introducing DNA into them, which has been reported for *Bacillus subtilis* (Duncan, C. H., Wilson, G. A. and Young, E E., Gene, 1, 153 (1977)). Also applicable is a method of making DNA recipient cells into protoplasts or spheroplasts, which can easily take up a recombinant DNA, and introducing a recombinant DNA. This method has been reported for *Bacillus subtilis*, actinomycetes, and yeasts (Chang, S, and Choen, S. N., Molec. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Acad. Sci. USA, 75, 1929 (1978)).

The copy number of the gltP and/or the gltS genes can also be increased by integrating multiple copies of the genes described above into a genomic DNA of a bacterium. In order to integrate multiple copies of the gltP and/or gltS genes into a genomic DNA of a bacterium, homologous recombination can be performed by targeting a sequence that is present in multiple copies on the genomic DNA, such as a repetitive DNA or inverted repeat present at the end of a transposable element. The gene may be ligated to the gltP gene and/or the gltS gene that is present in the genome in tandem, or the gene may also be introduced into an unnecessary gene in the genome so that the gene is present in a multiple number. Such gene transfer can be attained by using a temperature sensitive vector or an integration vector.

Alternatively, as disclosed in Japanese Patent Laid-open No. 2-109985, it is also possible to incorporate the gltP gene and/or the gltS gene into a transposon, and allow it to be transferred to introduce multiple copies of the gene into a genomic DNA. Whether the gene has been transferred into a genome can be confirmed by performing Southern hybridization using a part of the gltP gene and/or the gltS gene as a probe.

Furthermore, expression of the gltP gene and/or the gltS gene may also be increased according to the method described in WO00/18935. In this method, an expression control sequence, such as a promoter of the gltP gene and/or the gltS gene, can be replaced on a genomic DNA or a plasmid with a stronger promoter, modifying the sequences of the −35 region and the −10 region so that the sequences become consensus sequences, amplifying a regulator that increases expression of the gltP gene and/or the gltS gene, or deleting or attenuating a regulator that decreases expression of the gltP gene and/or the gltS gene. For example, the lac promoter, trp promoter, trc promoter, tac promoter, araBA promoter, lambda phage PR promoter and PL promoter, tet promoter, T7 promoter, Φ10 promoter, and so forth are known as strong promoters. A promoter derived from the promoter of the threonine operon of E. coli or the tac promoter can also be used.

A promoter region, RBS (ribosome binding sequence), or SD region of the gltP gene and/or the gltS gene can also be modified so as to become stronger by introducing a nucleotide substitution or the like. Examples of methods for evaluating the strength of a promoter and strong promoters are described in the paper of Goldstein et al. (Prokaryotic promoters in biotechnology, Biotechnol. Annu. Rev., 1, 105-128 (1995)), and so forth. In addition, it is known that substitution of several nucleotides in the spacer region between the ribosome binding site (RBS) and start codon, especially the sequence immediately upstream from the start codon, greatly affects mRNA translation efficiency, and therefore this sequence may be modified. Expression control regions of the gltP gene and/or the gltS gene such as the promoter may be identified by using a promoter probe vector or gene analysis software such as GENETYX. By such substitution or modification of the promoter as described above, expression of the gltP gene and/or the gltS gene can be enhanced. Substitution of an expression control sequence can also be attained by, for example, a method using a temperature sensitive plasmid or Red-driven integration (WO2005/010175).

The aforementioned descriptions concerning homologues of genes and proteins, and increase of gene expression can also be similarly applied to genes other than the gltP and gltS genes, for example, the gene used for imparting an L-amino acid-producing ability, the ybjE gene, and expression products thereof.

<2> Method for Producing L-Amino Acid

The method for producing an L-amino acid is characterized by culturing the bacterium in accordance with the presently disclosed subject matter in a medium to produce and accumulate an L-amino acid such as L-lysine, L-threonine, L-asparagine, L-aspartic acid, L-methionine, L-alanine, L-isoleucine, and L-homoserine in the medium, and collecting the L-amino acid from the medium or cells.

As the medium, media conventionally used for the production of L-amino acids by fermentation using bacteria can be used. That is, typical media containing a carbon source, a nitrogen source, inorganic ions, and optionally other organic components as required can be used. As the carbon source, saccharides such as glucose, sucrose, lactose, galactose, fructose, and hydrolysates of starches; alcohols such as glycerol and sorbitol; and organic acids such as fumaric acid, citric acid and succinic acid can be used. Glucose, fructose, or sucrose is a particular example of the carbon source. In addition, as for a strain not having sucrose-assimilating ability, if a sucrose assimilation gene is introduced into such a strain, it becomes possible to use sucrose as a carbon source (U.S. Pat. No. 5,175,107). As the nitrogen source, inorganic ammonium salts such as ammonium sulfate, ammonium chloride, and ammonium phosphate, organic nitrogen such as soybean hydrolysate, ammonia gas, aqueous ammonia, and so forth can be used. As for organic trace nutrient sources, the medium can contain the required substances such as vitamin $B_1$ and L-homoserine, yeast extract, and so forth in appropriate amounts. Other than the above, potassium phosphate, magnesium sulfate, iron ions, manganese ions and so forth are added in small amounts as required. In addition, the medium may be either a natural medium or a synthetic medium, so long as the medium contains a carbon source, a nitrogen source, and inorganic ions, and containing other organic trace components as required.

Moreover, an L-amino acid that improves growth and productivity may be added. In the case of L-lysine fermentation, L-threonine, L-homoserine, and/or L-isoleucine can be added, and in the case of L-threonine fermentation, L-isoleucine, L-lysine, L-homoserine, etc. can be added. The concentration after such additions can be about 0.01 to 10 g/L.

The culture can be performed for 1 to 7 days under aerobic conditions. The culture temperature can be 24 to 37° C., and pH during the culture can be 5 to 9. To adjust the pH, inorganic or organic acidic or alkaline substances, ammonia gas, and so forth can be used. Collection of the L-amino acid from the fermentation medium can usually be attained by a combination of known methods such as ion exchange or by precipitation. When the L-amino acid is accumulated in the cells, the cells can be disrupted with, for example, supersonic waves or the like, and the L-amino acid can be collected by the ion exchange resin method or the like from the supernatant obtained by removing the cells by centrifugation from a suspension in which the cells have been disrupted.

When a basic amino acid such as L-lysine is produced, fermentation can be performed by controlling the pH of the medium during culture to about 6.5 to 9.0, and the pH of the medium at the end of the culture to about 7.2 to 9.0. However, a period during the culture should be maintained where the medium contains 20 mM or more of bicarbonate ions and/or carbonate ions. This is done so these bicarbonate ions and/or carbonate ions can act as counter ions to the basic amino acid. As a result, the objective basic amino acid can then be collected (Japanese Patent Laid-open No. 2002-65287, U.S. Patent Published Application No. 2002/0025564, European Patent Laid-open No. 1813677).

When a microorganism is chosen that is able to produce a basic amino acid, the culture can occur under aerobic conditions, and carbonate ions, bicarbonate ions, or both can be used as the major counter ions of the basic amino acid. To provide carbonate ions and/or bicarbonate ions in an amount required to serve as counter ions to the basic amino acid, it is known that the pH of the medium should be controlled to about 6.5 to 9.0, 6.5 to 8.0 in another example, during the culture, and should be controlled to about 7.2 to 9.0 at the end of the culture. Also, the pressure in the fermentation tank should be controlled so that it is positive during fermentation, or carbon dioxide or a mixed gas containing carbon dioxide can be supplied into the medium (Japanese Patent Laid-open No. 2002-65287, U.S. Patent Published Application No. 2002/0025564, European Patent Laid-open No. 1813677).

Pressure in the fermentation tank may be controlled so that it is positive during the fermentation, and at the same time, carbon dioxide gas or a mixed gas containing carbon dioxide gas may be supplied to the medium. Both the above operations can be performed so that there is a period during the culture when 20 mM or more, 30 mM or more in another example, 40 mM or more in another example, of bicarbonate ions and/or carbonate ions are present in the medium. The internal pressure of the fermentation tank, the added amount of carbon dioxide or mixed gas containing carbon dioxide, or the limited gas supply volume can be determined by, for example, measuring bicarbonate ions or carbonate ions in the medium, or the pH or ammonia concentration of the medium.

As described above, the pH of the medium can be controlled to about 6.0 to 9.0, 6.5 to 8.0 in another example, during the culture, and about 7.2 to 9.0 at the end of the culture. The pH of the medium can be lowered as compared to the conventional methods, while ensuring the presence of bicarbonate ions and/or carbonate ions in an amount appropriate for their use as counter ions. When the pH is controlled with ammonia, ammonia can be supplied to increase the pH, and it can serve as a nitrogen source for the basic amino acid. Examples of cations other than the basic amino acid that can be present in the medium can include K, Na, Mg, Ca etc. These can be present in an amount of 50% or less of the total cations.

Furthermore, the internal pressure of the fermentation tank during fermentation can be made positive by, for example, making the gas supply pressure higher than the exhaust pressure. By making the internal pressure of the fermentation tank positive, the carbon dioxide generated by fermentation dissolves in the culture medium to generate bicarbonate ions or carbonate ions, and these can serve as counter ions of the basic amino acid. The internal pressure of the fermentation tank can be, specifically, 0.03 to 0.2 MPa, 0.05 to 0.15 MPa in another example, 0.1 to 0.3 MPa in another example, in terms of the gage pressure (pressure difference with respect to the atmospheric pressure). Moreover, by supplying carbon dioxide or a mixed gas containing carbon dioxide to the culture medium, carbon dioxide may be dissolved in the medium. Furthermore, when supplying carbon dioxide or a mixed gas containing carbon dioxide to the medium, the internal pressure of the fermentation tank may be adjusted to be positive.

The internal pressure of the fermentation tank may be adjusted to be positive by, for example, making the gas supply pressure higher than the exhaust pressure. Furthermore, when carbon dioxide is supplied to the medium, for example, pure carbon dioxide or a mixed gas containing 5% by volume or more of carbon dioxide may be bubbled in the medium.

The aforementioned methods for dissolving bicarbonate ions and/or carbonate ions in the medium may be used independently, or two or more of them may be used in combination.

In the conventional methods, a sufficient amount of ammonium sulfate or ammonium chloride is usually added to the medium to act as counter anions of the basic amino acid to be produced. Sulfuric acid or hydrochloric acid decomposition products of proteins etc. can also be added to the medium as a nutrient component, and thus sulfate ions and chloride ions generated from these are present in the medium. Therefore, the concentration of the weakly acidic carbonate ions is extremely low during the culture, for example, on the order of ppm. The above embodiment in accordance with the presently disclosed subject matter is characterized in that these sulfate ions and chloride ions are reduced, and the carbon dioxide released by the microorganism during fermentation is dissolved in the medium in the aforementioned fermentation environment and used as counter ions. Therefore, in accordance with the presently disclosed subject matter, sulfate or chloride ions are not required to be added to the medium in an amount more than the amount required for the growth. An appropriate amount of ammonium sulfate or the like can be added to the medium at an early stage of the culture, and then addition is stopped for a period in the middle of the culture. Alternatively, ammonium sulfate or the like may be added while maintaining the balance with the dissolved carbonate ions or bicarbonate ions in the medium. Moreover, as a nitrogen source of the basic amino acid, ammonia may be added to the medium. Ammonia may be supplied to the medium independently, or together with other gases.

Lower concentrations of anions other than bicarbonate ions and/or carbonate ions in the medium can be used so long as they are present in amounts that are required for the growth of the microorganism. Examples of such anions include chloride ions, sulfate ions, phosphate ions, ionized organic acids, hydroxide ions, and so forth. The total molar concentration of these other ions can be usually 900 mM or lower, 700 mM or lower in another example, 500 mM or lower in another example, 300 mM or lower in another example, 200 mM or lower in another example.

To reduce the necessary amounts of sulfate ions and/or chloride ions is one of the objects of the presently disclosed subject matter, and the total amount of sulfate ions or chloride ions, or both contained in the medium is usually 700 mM or lower, 500 mM or lower, 300 mM or lower in another example, 200 mM or lower in another example, 100 mM or lower in another example.

If ammonium sulfate is added to the medium as a counter ion source of a basic amino acid, carbon dioxide in the culture medium is usually eliminated by sulfate ions. However, in accordance with the presently disclosed subject matter, it is not necessary to add an excess amount of ammonium sulfate to the medium, and therefore carbon dioxide can be easily dissolved in the fermentation medium.

Furthermore, in accordance with the presently disclosed subject matter, the total ammonia concentration in the medium can be controlled to such an extent that "production of the basic amino acid is not inhibited". Exemplary conditions under which the basic amino acid is not inhibited include conditions resulting in a yield and/or productivity corresponding to 50% or more, for example, 70% or more in another example, or 90% or more in another example, of the yield and/or productivity obtainable in the production of the basic amino acid under optimal conditions. Specifically, the total ammonia concentration in the medium can be 300 mM or lower, 250 mM or lower in another example, 200 mM or lower in another example. The dissociation degree of the ammonia decreases as the pH increases. Non-dissociating ammonia is more toxic to bacteria as compared to ammonium ions. Therefore, the upper limit of the total ammonia concentration should be determined also depending on the pH of the culture medium. That is, as the pH of the culture medium increases, the acceptable total ammonia concentration decreases. Therefore, the aforementioned total ammonia concentration "which does not inhibit the basic amino acid production" can be determined for each specific pH value. However, the total ammonia concentration range that is acceptable at the highest pH level during the culture may be used as the upper limit of the total ammonia concentration throughout the entire culture period.

On the other hand, the total ammonia concentration which functions as a source of nitrogen required for growth of the microorganism and production of the basic substance is not particularly limited, and can be appropriately determined, so long as the reduced amount of the nitrogen source, which can result in continuous depletion of ammonia during the culture, does not reduce productivity of the objective substance by the microorganism. For example, the ammonia concentration can be measured over time during the culture, and if ammonia in the medium is depleted, a small amount of ammonia may be added to the medium. Although the total ammonia concentration after the addition of ammonia is not particularly limited, the total ammonia concentration may be, for example, 1 mM or higher, 10 mM or higher in another example, 20 mM or higher in another example.

The medium may be any medium so long as it contains a carbon source and a nitrogen source. For the method, in accordance with the presently disclosed subject matter, a batch culture, fed-batch culture, or continuous culture may be used.

The aforementioned fed-batch culture can refer to a culture method of feeding a medium continuously or intermittently into a vessel under culture, and not extracting the medium from the vessel before completion of culture. The continuous culture refers to a method of continuously or intermittently feeding a medium into a vessel under culture and extracting the medium from the vessel under culture (normally, in an amount equivalent to the medium fed). The term "starting medium" can mean a medium used for batch culture before the feed medium is fed in the fed-batch culture or continuous culture, and the term "feed medium" means a medium to be supplied to a fermenter when fed-batch culture or continuous culture is performed. The feed medium may contain all or just some of the components necessary for the growth of a microorganism. The term "fermentation medium" means a medium contained in a fermenter, and an objective substance is collected from this fermentation medium. Furthermore, the term "fermenter" means a vessel in which amino acid production is performed, and the shape thereof is not limited. A fermentation tank or a jar fermenter may be used. Furthermore, the volume of the fermenter is not limited so long as the objective substance can be produced and collected.

As the carbon source, saccharides such as glucose, glycerol, fructose, sucrose, maltose, mannose, galactose, starch hydrolysate and molasses can be used, and glucose and sucrose can be used. In addition, organic acids such as acetic acid and citric acid, and alcohols such as ethanol and methanol, can also be used independently or in combination with other carbon sources. Furthermore, a raw material of the carbon source can include cane molasses, beet molasses, high test molasses, citrus molasses and invert sugar, and hydrolysates of natural raw materials such as cellulose, starch, corn, cereal and tapioca may also be used. Furthermore, carbon dioxide dissolved in the culture medium can also be used as a carbon source. These carbon sources can be used in the starting medium and feed medium. The medium may contain one or two or more kinds of these carbon sources. Furthermore, the same carbon source may be used for the starting medium and the feed medium, or the carbon source of the feed medium may be different from that of the starting medium. For example, glucose may be used as a carbon source of the starting medium, while sucrose may be used as a carbon source of the feed medium.

As the nitrogen source, ammonia, ammonium salts such as ammonium sulfate, ammonium carbonate, ammonium chloride, ammonium phosphate, ammonium acetate and urea, nitrates and so forth can be used. Ammonia gas and aqueous ammonia used to adjust the pH can also be utilized as the nitrogen source. Furthermore, peptone, yeast extract, meat extract, malt extract, corn steep liquor, soybean hydrolysate and so forth can also be utilized. The medium may contain one or more kinds of these nitrogen sources. These nitrogen sources can be used for both the starting medium and the feed medium. Furthermore, the same nitrogen source can be used for both the starting medium and the feed medium, or the nitrogen source of the feed medium may be different from that of the starting medium.

Furthermore, the medium can contain a phosphorus source in addition to the carbon source and nitrogen source. As the phosphorus source, potassium dihydrogenphosphate, dipotassium hydrogenphosphate, phosphoric acid polymers such as pyrophosphoric acid and so forth can be used.

Furthermore, the medium may contain a growth promoting factor, such as a nutrient showing a growth promoting effect, in addition to the carbon source and nitrogen source. As the growth promoting factor, trace metals, amino acids, vitamins, fatty acids, nucleic acids as well as peptone, casamino acid, yeast extract, soybean protein degradation product, and so forth containing the foregoing substances can be used. In particular, in the case of aromatic amino acids and branched chain amino acids, the biosynthesis systems thereof are common, and therefore biosynthesis of an amino acid other than the objective amino acid of the microorganism may be attenuated as described later. In such a case, the amino acid in which the biosynthesis system is attenuated can be added to the medium. For example, when the objective amino acid is L-lysine, such an amino acid is L-methionine, L-threonine, or L-isoleucine.

Examples of the trace metals include iron, manganese, magnesium, calcium and so forth. Examples of the vitamins include vitamin $B_1$, vitamin $B_2$, vitamin $B_6$, nicotinic acid, nicotinic acid amide, vitamin $B_{12}$, pyridoxine, pantothenic acid and so forth. These growth promoting factors may be contained in either the starting medium or the feed medium.

Furthermore, when an auxotrophic mutant strain that requires an amino acid or the like for growth is used, a required nutrient can be supplemented to the medium. In particular, since L-amino acid biosynthetic pathways are often enhanced and L-amino acid degrading ability is often attenuated in the L-amino acid-producing bacteria as described later, one or more types of substances such as L-lysine, L-homoserine, L-isoleucine and L-methionine can be added. Similarly, a required substance can be added to the medium for nucleic acid-producing bacteria.

The starting medium and the feed medium may have the same or different medium composition. Furthermore, when the starting medium and the feed medium contain seed crystals, seed crystal concentrations may be the same or different. Furthermore, when the feed medium is fed at multiple stages, the compositions of the feed media may be the same or different.

The culture can be performed as aeration culture at a fermentation temperature of 20 to 45° C., or 30 to 42° C. in another example.

The L-amino acid can be collected from the medium after the culture by a combination of known collection methods, for example, ion exchange resin, precipitation, and other known methods. When the L-amino acid precipitates in the medium, it can be collected by centrifugation or filtration. Moreover, when the L-amino acid precipitates in the medium, the L-amino acid dissolving in the medium may be crystallized, and then the precipitated L-amino acid and the crystals may be isolated together.

The culture of the microorganism may be performed by a seed culture and a main culture in order to ensure accumulation of the objective L-amino acid at a certain level or higher. The seed culture may be performed as a shaking culture using a flask or the like or batch culture, and the main culture may be performed as a fed-batch culture, batch culture or continuous culture. Alternatively, both the seed culture and the main culture may be performed as batch culture. Furthermore, preculture may be performed once or two or more times before the seed culture and the main culture, with gradually increasing culture scale during these cultures.

In these culture methods, when the L-amino acid concentration reaches the intended level, a part of the L-amino acid may be extracted, and the medium may be newly added to repeat the culture. As the medium to be newly added, a medium containing a carbon source and a nutrient having a growth promoting effect (growth promoting factor) can be used. As the carbon source of the medium to be added, glucose, sucrose, and fructose can be used. As the growth promoting factor, nitrogen sources, phosphoric acid, amino acids, and so forth can be used. As the nitrogen source, ammonia, ammonium salts such as ammonium sulfate, ammonium carbonate, ammonium chloride, ammonium phosphate, ammonium acetate and urea, nitrates and so forth can be used. Furthermore, as the phosphoric acid source, potassium dihydrogenphosphate and dipotassium hydrogenphosphate can be used. As for amino acids, when an auxotrophic mutant strain is used, a required nutrient can be supplemented.

When fed-batch culture or continuous culture is performed, the feed medium may be intermittently added so that the supply of saccharide or nutrients is temporarily stopped. The supply of the feed medium can be stopped for, at maximum, for example, 30% or less, 20% or less in another example, 10% or less in another example, of the feeding time. When the feed medium is intermittently added, the feed medium may be initially added over a predetermined time, and the second and following additions may be controlled so that they are started when an increase in the pH or the level of dissolved oxygen concentration is detected by a computer upon depletion of the carbon source in the fermentation medium during an period in which the feed medium is not being added, and prior to a period when the medium is being added, and thus the substrate concentration in the culture tank is always automatically maintained at a low level (U.S. Pat. No. 5,912,113). The carbon source of the feed medium is the same as that described above. Furthermore, the feed medium can be one type of medium, or a mixture of two or more types of media. When two or more types of feed media are used, the media may be mixed and added by using one feed can, or they may be fed by using two or more feed cans.

When a fed-batch culture is performed, the feed medium can be added so that saccharide is added so that the amount of carbon source in the feed medium or the whole fermentation medium does not exceed 30 g/L, and it can be controlled to be 20 g/L or lower, or 10 g/L or lower in another example. In particular, the saccharide concentration can be controlled so that it is in the aforementioned concentration range at the end of the logarithmic growth phase of the microorganism and thereafter. The feed rate of the carbon source can be controlled by using the method described in U.S. Pat. No. 5,912,113. Furthermore, saccharide and phosphoric acid can be fed at such concentrations that saccharide and phosphoric acid act as limiting factors of the bacterial cell growth. Phosphoric acid can be present in the feed medium in an amount of 2 or lower, 1.5 or lower in another example, 1 or lower in another example, expressed in terms of the phosphorous/carbon (P/C) ratio (refer to U.S. Pat. No. 5,763,230).

When a continuous culture method is used, the medium may be extracted and added simultaneously, or a part of the medium may be extracted, and then the medium may be added. Furthermore, the method may also be a continuous culture method including recycling cells in which the culture medium containing an L-amino acid and bacterial cells is extracted, and only the cells are returned to the fermenter (refer to French Patent No. 2669935). As the method for continuously or intermittently feeding a nutrient source, the same method as used in the fed-batch culture is used.

When the culture medium is intermittently extracted, a part of the L-amino acid is extracted when the L-amino acid concentration reaches a predetermined level, and a fresh medium is added to continue the culture. Furthermore, the culture can be performed so that the final volume of the medium after adding the medium is equal to the volume of the culture medium before the extraction. The term "equal" means that the volume of the medium after adding the medium corresponds to about 93 to 107% of the volume of the medium before the extraction.

When the culture medium is continuously extracted, the extraction can be started at the same time as, or after, the addition of the nutrient medium. For example, within 5 hours, 3 hours in another example, 1 hour in another example, at maximum, after the start of the addition, the extraction can be started. Furthermore, the extraction volume of the culture medium can be equal to the volume of the medium added.

The continuous culture method, including recycling bacterial cells, is a method of intermittently or continuously extracting the fermentation medium when the L-amino acid concentration reaches a predetermined level, extracting only the L-amino acid, and re-circulating filtration residues containing bacterial cells or centrifugation supernatant into the fermentation vessel, and it can be performed by referring to, for example, French Patent No. 2669935.

Fermentation broth containing a basic amino acid obtained in accordance with the presently disclosed subject matter can include carbonate ions and/or bicarbonate ions so that the normality ratio represented by the following equation becomes 5 to 100%.

Normality ratio=(Normality of bicarbonate ions and/or carbonate ions)/(Normality of cations mainly consisting of basic amino acid)×100

The carbonate ions and bicarbonate ions in the medium are released as carbon dioxide upon heating, and the content of the basic amino acid in the solid content of the fermentation broth is thereby increased. Furthermore, since carbonates can be easily replaced with an acid stronger than carbonic acid by adding such an acid to the fermentation broth, various salt forms can be selected.

EXAMPLES

Hereafter, the present invention will be more specifically explained with reference to the following non-limiting examples.

Example 1

Construction of Plasmid for Enhancement of gltPp Gene or gltS Gene

The entire genomic nucleotide sequence of *Escherichia coli* K-12 strain has already been reported (Genbank Accession No. U00096, Science, 277, 1453-1474 (1997)). The plasmid vector pMW118 (Nippon Gene) was used to amplify the objective genes. This plasmid vector has a multi-cloning site for the cloning of arbitrary genes, and this site was used to clone and amplify the genes.

The reported nucleotide sequences of gltP and gltS genes in the genomic sequence of *Escherichia coli* and flanking regions thereof were used to design and synthesize the synthetic oligonucleotides shown in SEQ ID NOs: 8 and 9 for use as 5' and 3' primers, respectively, for PCR amplification of gltP, and the synthetic oligonucleotides shown in SEQ ID NOs: 10 and 11 for use as 5' and 3' primers, respectively, for PCR amplification of gltS. PCR was performed using these primers and the genomic DNA of the *Escherichia coli* K-12 MG1655 strain as the template to obtain gene fragments containing the gltP and gltS genes. The purified PCR products were blunt-ended, and then ligated with the vector pMW118 which had been digested with SmaI to construct the plasmid pMW-gltP for gltP amplification and the plasmid pMW-gltS for gltS amplification.

Example 2

Enhancement of ybjE Gene of WC196ΔcadAΔldcC Strain

The *Escherichia coli* WC196ΔcadAΔldcC strain described in International Patent Publication WO2006/078039 was used for its ability to produce L-lysine. This strain was derived from the *Escherichia coli* WC196 strain by disrupting the lysine decarboxylase genes cadA and ldcC using the Red-driven integration (Datsenko, K. A. and Wanner B. L., Proc. Natl. Acad. Sci. USA. 97:6640-6645 (2000)) and the excision system derived from λ phage (J. Bacteriol., 184: 5200-5203 (2002)) in combination. The resulting strain was deposited at the independent administrative agency, National Institute of Advanced Industrial Science and Technology, International Patent Organism Depository (Tsukuba Central 6, 1-1, Higashi 1-Chome, Tsukuba-shi, Ibaraki-ken, 305-8566, Japan) on Oct. 7, 2008, and given an accession number of FERM BP-11027.

It is known that the ability of the strain to produce L-lysine is improved by enhancing the activity of the YbjE protein, which has an L-lysine excretion activity (U.S. Patent Published Application No. 2006/0019355). Therefore, expression of the ybjE gene in the WC196ΔcadAΔldcC strain was enhanced by replacing a sequence upstream of the ybjE gene that includes the native promoter of the ybjE gene and the ribosome binding site (RBS) on the chromosome with an upstream sequence of the lac gene which includes the tac promoter.

The promoter of the ybjE gene and the RBS sequence of the WC196ΔcadAΔldcC strain was replaced by the aforementioned method using the Red-driven integration and an excision system derived from λ phage in combination. Specifically, the sequence that is 157 bp upstream from the start codon (nucleotide numbers 49 to 51) of the ybjE gene (SEQ ID NO: 5) was replaced with the sequence of SEQ ID NO: 7. Strains having the intended substitution can be selected by measuring kanamycin resistance, and can be confirmed by PCR. The resulting strain in which the native promoter of the ybjE gene and the RBS sequence were replaced was designated "WC196LCY".

Example 3

Effect of Amplification of gltP and gltS Genes in L-Lysine-Producing Strain of *Escherichia* Bacterium <3-1> Introduction of Plasmid for Lysine Production into WC196LCY Strain The WC196LCY strain was transformed with a plasmid for lysine production, pCABD2 (European Patent No. 0733710), carrying the dapA, dapB and lysC genes, in a conventional manner to obtain "WC196LCY/pCABD2". pCABD2 contains: 1) a DNA encoding dihydrodipicolinate synthase (DDPS) of *Escherichia coli* that is mutated so that it is desensitized to feedback inhibition by L-lysine, 2) a DNA encoding aspartokinase III of *Escherichia* which is also mutated so that it is desensitized to feedback inhibition by L-lysine, 3) a DNA encoding dihydrodipicolinate reductase of *Escherichia coli*, and 4) a DNA encoding diaminopimelate dehydrogenase of *Brevibacterium lactofermentum*.

WC196LCY/pCABD2 strains were separately transformed with the plasmids pMW-gltP and pMW-gltS, which were produced in Example 1, to obtain ampicillin resistant strains. After confirmation of the successful transformation of the above plasmids, cells with the plasmid pMW-gltP were designated "WC196LCY/pCABD2/pMW-gltP", and cells with the plasmid pMW-gltS were designated "WC196LCY/pCABD2/pMW-gltS". Moreover, a strain transformed with pMW118 was prepared as a control, and designated "WC196LCY/pCABD2/pMW118".

Each of the strains produced above was cultured at 37° C. in LB medium containing 25 mg/L of streptomycin and 100 mg/L of ampicillin until the $OD_{600}$ of the culture became about 0.6, then an equal volume of a 40% glycerol solution was added to the culture, and the mixture was stirred, divided into appropriate volumes and stored at −80° C. as glycerol stocks.

<3-2> Lysine Production Culture

The above glycerol stocks were thawed, uniformly applied in a volume of 500 μL each to an L-plate containing 25 mg/L of streptomycin and 100 mg/L of ampicillin, and cultured at 37° C. for 24 hours. About ⅛ of the cells contained on one plate were inoculated into 20 mL of the fermentation medium described below containing 25 mg/L of streptomycin and 100 mg/L of ampicillin in a 500 ml-volume Sakaguchi flask, and cultured at 37° C. for 22 hours on a reciprocally shaking culture apparatus. After the culture, the amounts of L-lysine and L-glutamic acid that had accumulated in the medium were measured with a Biotec Analyzer AS210 (SAKURA SEIKI). The composition of the medium used for the culture is shown below.

L-Lysine Production Medium:

| | |
|---|---|
| Glucose | 40 g/L |
| $(NH_4)_2SO_4$ | 24 g/L |
| $KH_2PO_4$ | 1.0 g/L |
| $MgSO_4 \cdot 7H_2O$ | 1.0 g/L |
| $FeSO_4 \cdot 7H_2O$ | 0.01 g/L |
| $MnSO_4 \cdot 7H_2O$ | 0.08 g/L |
| Yeast Extract | 2.0 g/L |
| L-Isoleucine | 0.1 g/L |
| NaCl | 1.0 g/L |
| $CaCO_3$ | 50 g/L |

(Japanese Pharmacopoeia)

The medium was adjusted to pH 7.0 with KOH, and autoclaved at 115° C. for 10 minutes, except that glucose and $MgSO_4 \cdot 7H_2O$ were mixed and autoclaved separately from the other components. $CaCO_3$ was added after hot air sterilization.

The L-lysine yields and L-glutamic acid concentrations observed after 22 hours of the culture are shown in Table 3 with relative values based on the values observed for the control WC196LCY/pCABD2/pMW118, which are taken as 100.

TABLE 3

Effect of amplification of gltP or gltS in L-lysine-producing bacterium, WC196LCY/pCABD2

| Strain | L-Lysine yield (relative value) | L-Glutamic acid concentration (relative value) |
|---|---|---|
| WC196LCY/pCABD2/pMW118 | 100 | 100 |
| WC196LCY/pCABD2/pMW-gltP | 99 | 47 |
| WC196LCY/pCABD2/pMW-gltS | 100 | 55 |

In the gltP gene-amplified strain WC196LCY/pCABD2/pMW-gltP and the gltS gene-amplified strain WC196LCY/pCABD2/pMW-gltS, the by-production amount of L-glutamic acid decreased as compared to that of the control WC196LC/pCABD2/pMW118 without reducing the L-lysine yield.

Example 4

Effect of Amplification of gltP or gltS Gene in L-Threonine-Producing Strain of *Escherichia* Bacterium The *Escherichia coli* VKPM B-3996 strain (refer to U.S. Pat. No. 5,175,107) was used for its ability to produce L-threonine.

Cells of the B-3996 strain were transformed separately with plasmids pMW-gltP and pMW-gltS, which were produced in Example 1, to obtain ampicillin resistant strains. After confirmation of the successful transformation of the above plasmids, cells with the plasmid pMW-gltP were designated "B-3996/pMW-gltP", and cells with the plasmid pMW-gltS were designated "B-3996/pMW-gltS". Moreover, a strain transformed with pMW118 was prepared as a control, and designated "B-3996/pMW118".

Each of the strains produced above was cultured at 37° C. in LB medium containing 100 mg/L of ampicillin and 20 mg/L of streptomycin sulfate until the $OD_{600}$ of the culture became about 0.6, then an equal volume of a 40% glycerol solution was added to the culture, and the mixture was stirred, then divided into appropriate volumes and stored at −80° C. as glycerol stocks.

The above glycerol stocks were thawed, uniformly applied in a volume of 150 µL each to an L-plate containing 100 mg/L of ampicillin and 20 mg/L of streptomycin sulfate, and cultured at 37° C. for 24 hours. About 1/10 of the cells contained on one plate were inoculated into 50 mL of LB medium containing 100 mg/L of ampicillin and 20 mg/L of streptomycin sulfate in a baffled flask, and cultured at 40° C. for 4 hours at 144 rpm to form a seed culture.

After completion of the seed culture, 30 ml (about 10% of the main cuture medium) of the seed culture medium was inoculated into 300 mL of the main culture medium described below in a 1 L-volume jar fermenter, and cultured at 40° C. and pH 7.0.

Composition of Main Culture Medium:

| | |
|---|---|
| Glucose | 100 g/L |
| Yeast Extract | 1.8 g/L |
| $KH_2PO_4$ | 1.0 g/L |
| NaCl | 0.6 g/L |
| $MgSO_4 \cdot 7H_2O$ | 0.36 g/L |
| $FeSO_4 \cdot 7H_2O$ | 18 mg/L |
| $MnSO_4 \cdot 4H_2O$ | 18 mg/L |
| Streptomycin sulfate | 20 mg/L |
| Ampicillin | 100 mg/L |

Glucose and $MgSO_4.7H_2O$ were mixed, and sterilized separately from the other components.

During the culture, the culture medium was adjusted to pH 7.0 by adding ammonia gas.

After the culturing for 15.5 hours, the concentration of L-threonine that had accumulated in the medium was measured by HPLC. Moreover, the amount of L-glutamic acid was measured with a Biotec Analyzer AS210 (SAKURA SEIKI). The L-threonine yields and L-glutamic acid concentrations are shown in Table 4 with relative values based on the values observed for the control B-3996/pMW118, which are taken as 100.

TABLE 4

Effect of amplification of gltP or gltS in L-threonine-producing bacterium B-3996

| Strain | L-Threonine yield (relative value) | L-Glutamic acid concentration (relative value) |
|---|---|---|
| B-3996/pMW118 | 100.0 | 100.0 |
| B-3996/pMW-gltP | 103.0 | 13.4 |
| B-3996/pMW-gltS | 99.4 | 13.4 |

In the gltP gene-amplified strain B-3996/pMW-gltP and the gltS gene-amplified strain B-3996/pMW-gltS, the by-production amount of L-glutamic acid decreased as compared to that of the control B-3996/pMW118 without reducing L-threonine yield.

Example 5

Comparison of Effect of Amplification of gltP or gltS Gene and Effect of Amplification of gadC Gene in L-Threonine-Producing Strain of *Escherichia* Bacterium It is known that by simultaneously amplifying the gadC gene, which encodes a protein having L-glutamate/GABA anti-porter activity, and the gadB gene, which encodes a protein having glutamate decarboxylase activity, the production of L-lysine, L-threonine, and L-tryptophan is improved (WO2008/044453). Therefore, the effect of amplifying the gltP or gltS genes on reducing the amount of glutamic acid was compared with the effect of amplifying the gadC gene.

The plasmid pMWPthr described in WO2008/044453 was used to construct a plasmid for amplifying gadC. This plasmid is derived from the vector pMW118 (Nippon Gene) by inserting the promoter region of the threonine operon (thrABC) from the genome of *Escherichia coli* between the HindIII site and the XbaI site. In this way, amplification of a gene inserted downstream from the promoter in enabled.

The reported nucleotide sequence of the gadC gene in the genome sequence of *Escherichia coli* and flanking regions thereof were used to design and synthesize the synthetic oligonucleotides shown in SEQ ID NOs: 14 and 15 for use as 5' and 3' primers, respectively, for PCR amplification of gadC. These primers were used with genomic DNA of the *Escherichia coli* K-12 W3110 strain as the template to perform PCR and thereby obtain a gene fragment containing the gadC gene. The purified PCR product was digested with SacI and SmaI, and then ligated with the vector pMWPthr that had been digested with SacI and SmaI to construct the plasmid pMW-gadC for gadC amplification.

In the same manner as that of Example 4, the B-3996 strain was transformed with pMW-gadC, and the obtained transformant was designated "B-3996/pMW-gadC". This strain was cultured together with B-3996/pMW118, B-3996/pMW-gltP, and B-3996/pMW-gltS in the same manner as that of Example 4. Concentrations of L-glutamic acid that had accumulated in the medium are shown in Table 5 in terms of relative values based on the value observed with the control B3996/pMW118, which is taken as 100.

TABLE 5

Comparison of effect of amplification of gltP or gltS gene and effect of amplification of gadC in L-threonine-producing bacterium strain B-3996

| Strain | L-Glutamic acid concentration (relative value) |
|---|---|
| B-3996/pMW118 | 100.0 |
| B-3996/pMW-gltP | 13.4 |
| B-3996/pMW-gltS | 13.4 |
| B-3996/pMW-gadC | 109.3 |

In the gltP gene-amplified strain B-3996/pMW-gltP and the gltS gene-amplified strain B-3996/pMW-gltS, the amount of L-glutamic acid produced as a by-product was markedly decreased. In the gadC-amplified strain B-3996/pMW-gadC, L-glutamic acid concentration did not decrease, but increased conversely, and thus gadC amplification did not have the effect of reducing L-glutamic acid concentration in the fermentation medium.

EXPLANATION OF SEQUENCE LISTING

SEQ ID NO: 1: gltP gene sequence
SEQ ID NO: 2: GltP amino acid sequence
SEQ ID NO: 3: gltS gene sequence
SEQ ID NO: 4: GltS amino acid sequence
SEQ ID NO: 5: ybjE gene sequence
SEQ ID NO: 6: YbjE amino acid sequence
SEQ ID NO: 7: ybjE upstream sequence for substitution
SEQ ID NO: 8: Primer for gltP amplification (5' side)
SEQ ID NO: 9: Primer for gltP amplification (3' side)
SEQ ID NO: 10: Primer for gltS amplification (5' side)
SEQ ID NO: 11: Primer for gltS amplification (3' side)
SEQ ID NO: 12: gltP conserved sequence
SEQ ID NO: 13: gltS conserved sequence
SEQ ID NO: 14: Primer for gadC amplification (5' side)
SEQ ID NO: 15: Primer for gadC amplification (3' side)

INDUSTRIAL APPLICABILITY

By using the method of the present invention, by-products can be reduced in production of L-lysine, L-threonine, L-asparagine, L-aspartic acid, L-methionine, L-alanine, L-isoleucine, and L-homoserine by fermentation.

What is claimed is:

1. A method for producing an L-amino acid comprising culturing a bacterium in a medium, wherein said bacterium belongs to the family Enterobacteriaceae and is able to produce L-amino acid, and collecting the L-amino acid from the medium, wherein:

the bacterium has been modified so that expression of a gltP and/or gltS gene(s) from an Enterobacteriaceae bacterium is/are increased compared to a non-modified bacterium by a method selected from the group consisting of:
- a) increasing copy number of the gene(s),
- b) modifying an expression control sequence of the gene(s), and
- c) combinations thereof, and the L-amino acid is selected from the group consisting of L-lysine, L-threonine, L-asparagine, L-aspartic acid, L-methionine, L-alanine, L-isoleucine, and L-homoserine.

2. The method according to claim 1, wherein the gltP gene encodes a protein selected from the group consisting of:
(A) a protein comprising the amino acid sequence shown in SEQ ID NO: 12, and
(B) a protein comprising the amino acid sequence shown in SEQ ID NO: 12, but wherein one to five amino acid residues are substituted, deleted, inserted, added or inverted, and said protein has L-glutamate transporter activity.

3. The method according to claim 1, wherein the gltP gene encodes a protein selected from the group consisting of:
(A) a protein comprising the amino acid sequence shown in SEQ ID NO: 2, and
(B) a protein comprising the amino acid sequence shown in SEQ ID NO: 2, but wherein one to five amino acid residues are substituted, deleted, inserted, added or inverted, and said protein has L-glutamate transporter activity.

4. The method according to claim 1, wherein the gltP gene comprises a DNA selected from the group consisting of:
(A) a DNA comprising the nucleotide sequence shown in SEQ ID NO: 1, and
(B) a DNA which is able to hybridize with a sequence complementary to the nucleotide sequence shown in SEQ ID NO: 1, under stringent conditions comprising washing at 60° C. at a salt concentration of 0.1×SSC and 0.1% SDS, and which encodes a protein which has L-glutamate transporter activity.

5. The method according to claim 1, wherein the gltS gene encodes a protein selected from the group consisting of:
(A) a protein comprising the amino acid sequence shown in SEQ ID NO: 13, and
(B) a protein comprising the amino acid sequence shown in SEQ ID NO: 13, but wherein one to five amino acid residues are substituted, deleted, inserted, added or inverted, and said protein has L-glutamate transporter activity.

6. The method according to claim 1, wherein the gltS gene encodes a protein selected from the group consisting of:
(A) a protein comprising the amino acid sequence shown in SEQ ID NO: 4, and
(B) a protein comprising the amino acid sequence shown in SEQ ID NO: 4, but wherein one to five amino acid residues are substituted, deleted, inserted, added or inverted, and said protein has L-glutamate transporter activity.

7. The method according to claim 1, wherein the gltS gene is selected from the group consisting of:
(A) a DNA comprising the nucleotide sequence shown in SEQ ID NO: 3, and
(B) a DNA which is able to hybridize with a sequence complementary to the nucleotide sequence shown in SEQ ID NO: 3, under stringent conditions comprising washing at 60° C. at a salt concentration of 0.1×SSC and 0.1% SDS, and which encodes a protein having an L-glutamate transporter activity.

8. The method according to claim 1, wherein the L-amino acid is L-lysine, and expression of a ybjE gene from an Enterobacteriaceae bacterium is increased in the bacterium.

9. The method according to claim 8, wherein the ybjE gene encodes a protein selected from the group consisting of:
(A) a protein comprising the amino acid sequence shown in SEQ ID NO: 6,
(B) a protein comprising the amino acid sequence of the amino acid numbers 17 to 315 in SEQ ID NO: 6,
(C) a protein comprising the amino acid sequence shown in SEQ ID NO: 6 but wherein one to five amino acid residues are substituted, deleted, inserted, added or inverted, and said protein has an L-lysine excretion activity, and
(D) a protein comprising the amino acid sequence of the amino acid numbers 17 to 315 in SEQ ID NO: 6, but wherein one to five amino acid residues are substituted, deleted, inserted, added or inverted, and said protein has an L-lysine excretion activity.

10. The method according to claim 8, wherein the ybjE gene is a DNA selected from the group consisting of:
(A) a DNA comprising the nucleotide sequence shown in SEQ ID NO: 5,
(B) a DNA comprising the nucleotide sequence of the nucleotide numbers 49 to 948 in SEQ ID NO: 5,
(C) a DNA which is able to hybridize with a sequence complementary to the nucleotide sequence shown in SEQ ID NO: 5, under stringent conditions comprising washing at 60° C. at a salt concentration of 0.1×SSC and 0.1% SDS, and which encodes a protein having an L-lysine excretion activity, and
(D) a DNA which is able to hybridize with a sequence complementary to the nucleotide sequence of the nucleotide numbers 49 to 948 in SEQ ID NO: 5, under stringent conditions comprising washing at 60° C. at a salt concentration of 0.1×SSC and 0.1% SDS, and which encodes a protein having an L-lysine excretion activity.

11. The method according to claim 1, wherein the L-amino acid is L-lysine, pH of the medium is controlled to be 6.0 to 9.0 during culture for the production, and 7.2 to 9.0 at the end of the culture, and there is a culture period when 20 mM or more of bicarbonate ions and/or carbonate ions are present in the medium so that the bicarbonate ions and/or carbonate ions act as counter ions of the basic amino acid.

12. The method according to claim 1, wherein the bacterium is an *Escherichia bacterium*.

13. The method according to claim 12, wherein the bacterium is *Escherichia coli*.

* * * * *

SEQUENCE LISTING

```
<160> NUMBER OF SEQ ID NOS: 15

<210> SEQ ID NO 1
<211> LENGTH: 1314
<212> TYPE: DNA
<213> ORGANISM: Escherichia coli
<220> FEATURE:
<221> NAME/KEY: CDS
<222> LOCATION: (1)..(1314)

<400> SEQUENCE: 1 atg aaa aat ata aaa ttc agc ctg gcc tgg cag att ctg ttt gct atg        48
Met Lys Asn Ile Lys Phe Ser Leu Ala Trp Gln Ile Leu Phe Ala Met
1               5                   10                  15 gtg ctg ggc att ctc ctg gga agc tac ctg cac tac cat agc gac agc        96
Val Leu Gly Ile Leu Leu Gly Ser Tyr Leu His Tyr His Ser Asp Ser
                20                  25                  30 cgc gac tgg ctg gtc gtc aat ttg ctc tct ccg gcg ggt gat atc ttc       144
Arg Asp Trp Leu Val Val Asn Leu Leu Ser Pro Ala Gly Asp Ile Phe
            35                  40                  45 atc cat ctg att aaa atg att gtt gtg ccg att gtg atc tcc acg ctg       192
Ile His Leu Ile Lys Met Ile Val Val Pro Ile Val Ile Ser Thr Leu
        50                  55                  60 gtg gtg ggt atc gcg ggt gtt ggt gat gcc aaa cag ctc ggg cgt att       240
Val Val Gly Ile Ala Gly Val Gly Asp Ala Lys Gln Leu Gly Arg Ile
65                  70                  75                  80 ggc gcg aaa acc att atc tac ttc gag gtg atc acc acc gtc gcc atc       288
Gly Ala Lys Thr Ile Ile Tyr Phe Glu Val Ile Thr Thr Val Ala Ile
                85                  90                  95 att ttg ggg atc act ctg gcg aac gtc ttc cag ccc ggt gcc ggg gtg       336
Ile Leu Gly Ile Thr Leu Ala Asn Val Phe Gln Pro Gly Ala Gly Val
                100                 105                 110 gat atg tcg cag ttg gcg acc gtc gat atc tcg aaa tat cag agc act       384
Asp Met Ser Gln Leu Ala Thr Val Asp Ile Ser Lys Tyr Gln Ser Thr
            115                 120                 125 acg gaa gcg gta caa agc agt tcc cac ggc att atg ggc acg att ttg       432
Thr Glu Ala Val Gln Ser Ser Ser His Gly Ile Met Gly Thr Ile Leu
        130                 135                 140
```

```
tcg ctg gtg ccg acg aac att gtg gcg tcg atg gcg aaa ggc gaa atg       480
Ser Leu Val Pro Thr Asn Ile Val Ala Ser Met Ala Lys Gly Glu Met
145                 150                 155                 160 ctg ccg atc atc ttt ttc tcg gtg ctg ttt ggt ctg ggg ctt tct tcc       528
Leu Pro Ile Ile Phe Phe Ser Val Leu Phe Gly Leu Gly Leu Ser Ser
                165                 170                 175 ctg ccc gcg acg cat cgt gaa ccg ctg gtg acc gtg ttc cgc tcc atc       576
Leu Pro Ala Thr His Arg Glu Pro Leu Val Thr Val Phe Arg Ser Ile
            180                 185                 190 tct gaa acc atg ttt aaa gtg act cac atg gtg atg cgt tat gca ccg       624
Ser Glu Thr Met Phe Lys Val Thr His Met Val Met Arg Tyr Ala Pro
        195                 200                 205 gtg ggt gtg ttt gcg ctg att gcg gtg acg gtg gct aac ttt ggt ttc       672
Val Gly Val Phe Ala Leu Ile Ala Val Thr Val Ala Asn Phe Gly Phe
    210                 215                 220 tcg tct ctg tgg cca ctg gcg aaa ctg gtg ctg ctg gtg cat ttc gcc       720
Ser Ser Leu Trp Pro Leu Ala Lys Leu Val Leu Leu Val His Phe Ala
225                 230                 235                 240 att ctg ttc ttc gcg ctg gta gtg ctg gga att gtg gcg cgc ctg tgc       768
Ile Leu Phe Phe Ala Leu Val Val Leu Gly Ile Val Ala Arg Leu Cys
                245                 250                 255 ggg tta agc gtc tgg atc ctg att cgt att ctg aaa gat gag ctg att       816
Gly Leu Ser Val Trp Ile Leu Ile Arg Ile Leu Lys Asp Glu Leu Ile
            260                 265                 270 ctg gcg tac tcc act gcc agc tct gaa agc gtg ctg ccg cga att att       864
Leu Ala Tyr Ser Thr Ala Ser Ser Glu Ser Val Leu Pro Arg Ile Ile
        275                 280                 285 gag aag atg gaa gcc tac gga gca ccg gtg tcg atc acc agt ttc gtg       912
Glu Lys Met Glu Ala Tyr Gly Ala Pro Val Ser Ile Thr Ser Phe Val
    290                 295                 300 gtg ccg acc ggt tac tct ttt aac ctt gat ggt tcg acg ctg tat caa       960
Val Pro Thr Gly Tyr Ser Phe Asn Leu Asp Gly Ser Thr Leu Tyr Gln
305                 310                 315                 320 agt att gcc gct atc ttc atc gcg cag ttg tat ggc att gac ctg tcc      1008
Ser Ile Ala Ala Ile Phe Ile Ala Gln Leu Tyr Gly Ile Asp Leu Ser
                325                 330                 335 atc tgg cag gaa atc att ctg gtg ctg acg ctg atg gtg acc tcg aaa      1056
Ile Trp Gln Glu Ile Ile Leu Val Leu Thr Leu Met Val Thr Ser Lys
            340                 345                 350 ggg att gct ggc gtg cct ggc gtg tcg ttt gtg gtg ttg ctg gca acg      1104
Gly Ile Ala Gly Val Pro Gly Val Ser Phe Val Val Leu Leu Ala Thr
        355                 360                 365 ctg ggt agc gta ggt att ccg ctg gaa ggt ctg gcg ttt att gct ggt      1152
Leu Gly Ser Val Gly Ile Pro Leu Glu Gly Leu Ala Phe Ile Ala Gly
    370                 375                 380 gtt gac cgt atc ctc gac atg gcg cgt act gcg ctg aac gtg gtg ggt      1200
Val Asp Arg Ile Leu Asp Met Ala Arg Thr Ala Leu Asn Val Val Gly
385                 390                 395                 400 aat gcg ctg gcg gtg ctg gtg att gcc aag tgg gaa cac aaa ttt gac      1248
Asn Ala Leu Ala Val Leu Val Ile Ala Lys Trp Glu His Lys Phe Asp
                405                 410                 415 cgt aag aaa gcg ctg gct tat gag cgt gaa gtg ctg ggc aaa ttt gat      1296
Arg Lys Lys Ala Leu Ala Tyr Glu Arg Glu Val Leu Gly Lys Phe Asp
            420                 425                 430 aaa act gcg gat caa taa                                              1314
Lys Thr Ala Asp Gln
        435
```

<210> SEQ ID NO 2
<211> LENGTH: 437

```
<212> TYPE: PRT
<213> ORGANISM: Escherichia coli

<400> SEQUENCE: 2
```

Met Lys Asn Ile Lys Phe Ser Leu Ala Trp Gln Ile Leu Phe Ala Met
1               5                   10                  15

Val Leu Gly Ile Leu Leu Gly Ser Tyr Leu His Tyr His Ser Asp Ser
            20                  25                  30

Arg Asp Trp Leu Val Val Asn Leu Ser Pro Ala Gly Asp Ile Phe
        35                  40                  45

Ile His Leu Ile Lys Met Ile Val Pro Ile Val Ser Thr Leu
        50                  55                  60

Val Val Gly Ile Ala Gly Val Gly Asp Ala Lys Gln Leu Gly Arg Ile
65              70                  75                  80

Gly Ala Lys Thr Ile Ile Tyr Phe Glu Val Ile Thr Thr Val Ala Ile
                85                  90                  95

Ile Leu Gly Ile Thr Leu Ala Asn Val Phe Gln Pro Gly Ala Gly Val
                100                 105                 110

Asp Met Ser Gln Leu Ala Thr Val Asp Ile Ser Lys Tyr Gln Ser Thr
            115                 120                 125

Thr Glu Ala Val Gln Ser Ser Ser His Gly Ile Met Gly Thr Ile Leu
130                 135                 140

Ser Leu Val Pro Thr Asn Ile Val Ala Ser Met Ala Lys Gly Glu Met
145                 150                 155                 160

Leu Pro Ile Ile Phe Phe Ser Val Leu Phe Gly Leu Gly Leu Ser Ser
                165                 170                 175

Leu Pro Ala Thr His Arg Glu Pro Leu Val Thr Val Phe Arg Ser Ile
            180                 185                 190

Ser Glu Thr Met Phe Lys Val Thr His Met Val Met Arg Tyr Ala Pro
            195                 200                 205

Val Gly Val Phe Ala Leu Ile Ala Val Thr Val Ala Asn Phe Gly Phe
210                 215                 220

Ser Ser Leu Trp Pro Leu Ala Lys Leu Val Leu Leu Val His Phe Ala
225                 230                 235                 240

Ile Leu Phe Phe Ala Leu Val Val Leu Gly Ile Val Ala Arg Leu Cys
                245                 250                 255

Gly Leu Ser Val Trp Ile Leu Ile Arg Ile Leu Lys Asp Glu Leu Ile
            260                 265                 270

Leu Ala Tyr Ser Thr Ala Ser Ser Glu Ser Val Leu Pro Arg Ile Ile
            275                 280                 285

Glu Lys Met Glu Ala Tyr Gly Ala Pro Val Ser Ile Thr Ser Phe Val
290                 295                 300

Val Pro Thr Gly Tyr Ser Phe Asn Leu Asp Gly Ser Thr Leu Tyr Gln
305                 310                 315                 320

Ser Ile Ala Ala Ile Phe Ile Ala Gln Leu Tyr Gly Ile Asp Leu Ser
                325                 330                 335

Ile Trp Gln Glu Ile Ile Leu Val Leu Thr Leu Met Val Thr Ser Lys
            340                 345                 350

Gly Ile Ala Gly Val Pro Gly Val Ser Phe Val Val Leu Leu Ala Thr
                355                 360                 365

Leu Gly Ser Val Gly Ile Pro Leu Glu Gly Leu Ala Phe Ile Ala Gly
            370                 375                 380

Val Asp Arg Ile Leu Asp Met Ala Arg Thr Ala Leu Asn Val Val Gly
385                 390                 395                 400

```
Asn Ala Leu Ala Val Leu Val Ile Ala Lys Trp Glu His Lys Phe Asp
            405                 410                 415

Arg Lys Lys Ala Leu Ala Tyr Glu Arg Glu Val Leu Gly Lys Phe Asp
            420                 425                 430

Lys Thr Ala Asp Gln
        435

<210> SEQ ID NO 3
<211> LENGTH: 1206
<212> TYPE: DNA
<213> ORGANISM: Escherichia coli
<220> FEATURE:
<221> NAME/KEY: CDS
<222> LOCATION: (1)..(1206)

<400> SEQUENCE: 3 atg ttt cat ctc gat act tta gca acg ctt gtt gcc gca acg ctg acg      48
Met Phe His Leu Asp Thr Leu Ala Thr Leu Val Ala Ala Thr Leu Thr
1               5                   10                  15 ttg ctg ctc ggg cgt aag ttg gtc cat tcc gtc tcc ttt ttg aag aaa      96
Leu Leu Leu Gly Arg Lys Leu Val His Ser Val Ser Phe Leu Lys Lys
            20                  25                  30 tac acc ata ccg gaa cct gtt gcg ggt ggt ttg ttg gtg gcg ctg gcg     144
Tyr Thr Ile Pro Glu Pro Val Ala Gly Gly Leu Leu Val Ala Leu Ala
        35                  40                  45 cta cta gta ctg aaa aaa agc atg ggc tgg gaa gtc aac ttt gat atg     192
Leu Leu Val Leu Lys Lys Ser Met Gly Trp Glu Val Asn Phe Asp Met
    50                  55                  60 tcc ctg cgc gat ccg tta atg ctg gct ttc ttc gcc acc att ggc ctg     240
Ser Leu Arg Asp Pro Leu Met Leu Ala Phe Phe Ala Thr Ile Gly Leu
65                  70                  75                  80 aac gcc aac att gcc agt ttg cgt gcc ggt ggg cgt gtg gtt ggc atc     288
Asn Ala Asn Ile Ala Ser Leu Arg Ala Gly Gly Arg Val Val Gly Ile
                85                  90                  95 ttc ttg att gtg gtt gtt ggt ctg ttg gtg atg caa aat gcc att ggc     336
Phe Leu Ile Val Val Val Gly Leu Leu Val Met Gln Asn Ala Ile Gly
            100                 105                 110 att ggt atg gct agc ttg tta ggg ctt gat ccg ctg atg ggg ctg ttg     384
Ile Gly Met Ala Ser Leu Leu Gly Leu Asp Pro Leu Met Gly Leu Leu
        115                 120                 125 gcc ggt tct att act ctt tcc ggc ggt cac ggt acg ggc gct gcg tgg     432
Ala Gly Ser Ile Thr Leu Ser Gly Gly His Gly Thr Gly Ala Ala Trp
    130                 135                 140 agt aaa ttg ttc att gaa cgt tat ggc ttc acc aat gcg acg gaa gtg     480
Ser Lys Leu Phe Ile Glu Arg Tyr Gly Phe Thr Asn Ala Thr Glu Val
145                 150                 155                 160 gcg atg gcc tgt gca acg ttc ggt ctg gtg ctg ggc ggt ttg att ggc     528
Ala Met Ala Cys Ala Thr Phe Gly Leu Val Leu Gly Gly Leu Ile Gly
                165                 170                 175 ggt ccg gtg gcg cgc tat ctg gtg aaa cac tcc acc acg ccg aac ggt     576
Gly Pro Val Ala Arg Tyr Leu Val Lys His Ser Thr Thr Pro Asn Gly
            180                 185                 190 att ccg gat gac cag gaa gtc ccg acg gcg ttt gaa aag ccg gat gtg     624
Ile Pro Asp Asp Gln Glu Val Pro Thr Ala Phe Glu Lys Pro Asp Val
        195                 200                 205 gga cgc atg atc acc tcg ttg gtg ctg att gaa act atc gcg ctg att     672
Gly Arg Met Ile Thr Ser Leu Val Leu Ile Glu Thr Ile Ala Leu Ile
    210                 215                 220 gct atc tgc ctg acg gtg ggg aaa att gtt gcg caa ctt ttg gct ggc     720
Ala Ile Cys Leu Thr Val Gly Lys Ile Val Ala Gln Leu Leu Ala Gly
225                 230                 235                 240
```

```
act gct ttt gaa ctg ccg acc ttc gtc tgt gta ctg ttt gtt ggc gtg      768
Thr Ala Phe Glu Leu Pro Thr Phe Val Cys Val Leu Phe Val Gly Val
            245                 250                 255 att ctg agc aac ggt ctg tca ata atg ggc ttt tac cgc gtc ttt gag      816
Ile Leu Ser Asn Gly Leu Ser Ile Met Gly Phe Tyr Arg Val Phe Glu
        260                 265                 270 cgt gcg gta tcc gtg ctg ggt aac gta agc ttg tcg ttg ttc ctg gcg      864
Arg Ala Val Ser Val Leu Gly Asn Val Ser Leu Ser Leu Phe Leu Ala
    275                 280                 285 atg gcg ttg atg ggg ctg aaa ctg tgg gag ctg gct tcg ctg gcg ctg      912
Met Ala Leu Met Gly Leu Lys Leu Trp Glu Leu Ala Ser Leu Ala Leu
290                 295                 300 ccg atg ctg gcg att ctg gtg gta cag acc atc ttc atg gcg ttg tat      960
Pro Met Leu Ala Ile Leu Val Val Gln Thr Ile Phe Met Ala Leu Tyr
305                 310                 315                 320 gcc atc ttc gtt acc tgg cgc atg atg ggc aaa aac tac gat gcg gca     1008
Ala Ile Phe Val Thr Trp Arg Met Met Gly Lys Asn Tyr Asp Ala Ala
            325                 330                 335 gtg ctg gct gcg ggt cac tgt ggt ttt ggc ctc ggt gca acg cca acg     1056
Val Leu Ala Ala Gly His Cys Gly Phe Gly Leu Gly Ala Thr Pro Thr
        340                 345                 350 gca atc gcc aac atg cag gcg atc act gaa cgc ttt ggc ccg tcg cac     1104
Ala Ile Ala Asn Met Gln Ala Ile Thr Glu Arg Phe Gly Pro Ser His
    355                 360                 365 atg gcg ttt ttg gtg gtg ccg atg gtc ggt gcg ttc ttt atc gat atc     1152
Met Ala Phe Leu Val Val Pro Met Val Gly Ala Phe Phe Ile Asp Ile
370                 375                 380 gtc aat gcg ctg gta att aag ttg tat ttg atg ttg ccg att ttt gcc     1200
Val Asn Ala Leu Val Ile Lys Leu Tyr Leu Met Leu Pro Ile Phe Ala
385                 390                 395                 400 ggt taa                                                              1206
Gly

<210> SEQ ID NO 4
<211> LENGTH: 401
<212> TYPE: PRT
<213> ORGANISM: Escherichia coli

<400> SEQUENCE: 4

Met Phe His Leu Asp Thr Leu Ala Thr Leu Val Ala Ala Thr Leu Thr
1               5                   10                  15

Leu Leu Leu Gly Arg Lys Leu Val His Ser Val Ser Phe Leu Lys Lys
            20                  25                  30

Tyr Thr Ile Pro Glu Pro Val Ala Gly Gly Leu Leu Ala Leu Ala
        35                  40                  45

Leu Leu Val Leu Lys Lys Ser Met Gly Trp Glu Val Asn Phe Asp Met
50                  55                  60

Ser Leu Arg Asp Pro Leu Met Leu Ala Phe Phe Ala Thr Ile Gly Leu
65                  70                  75                  80

Asn Ala Asn Ile Ala Ser Leu Arg Ala Gly Gly Arg Val Val Gly Ile
                85                  90                  95

Phe Leu Ile Val Val Gly Leu Leu Val Met Gln Asn Ala Ile Gly
            100                 105                 110

Ile Gly Met Ala Ser Leu Leu Gly Leu Asp Pro Leu Met Gly Leu Leu
        115                 120                 125

Ala Gly Ser Ile Thr Leu Ser Gly Gly His Gly Thr Gly Ala Ala Trp
    130                 135                 140

Ser Lys Leu Phe Ile Glu Arg Tyr Gly Phe Thr Asn Ala Thr Glu Val
145                 150                 155                 160
```

```
Ala Met Ala Cys Ala Thr Phe Gly Leu Val Leu Gly Leu Ile Gly
            165                 170                 175

Gly Pro Val Ala Arg Tyr Leu Val Lys His Ser Thr Thr Pro Asn Gly
        180                 185                 190

Ile Pro Asp Asp Gln Glu Val Pro Thr Ala Phe Glu Lys Pro Asp Val
        195                 200                 205

Gly Arg Met Ile Thr Ser Leu Val Leu Ile Glu Thr Ile Ala Leu Ile
    210                 215                 220

Ala Ile Cys Leu Thr Val Gly Lys Ile Val Ala Gln Leu Leu Ala Gly
225                 230                 235                 240

Thr Ala Phe Glu Leu Pro Thr Phe Val Cys Val Leu Phe Val Gly Val
                245                 250                 255

Ile Leu Ser Asn Gly Leu Ser Ile Met Gly Phe Tyr Arg Val Phe Glu
                260                 265                 270

Arg Ala Val Ser Val Leu Gly Asn Val Ser Leu Ser Leu Phe Leu Ala
            275                 280                 285

Met Ala Leu Met Gly Leu Lys Leu Trp Glu Leu Ala Ser Leu Ala Leu
290                 295                 300

Pro Met Leu Ala Ile Leu Val Val Gln Thr Ile Phe Met Ala Leu Tyr
305                 310                 315                 320

Ala Ile Phe Val Thr Trp Arg Met Met Gly Lys Asn Tyr Asp Ala Ala
                325                 330                 335

Val Leu Ala Ala Gly His Cys Gly Phe Gly Leu Gly Ala Thr Pro Thr
                340                 345                 350

Ala Ile Ala Asn Met Gln Ala Ile Thr Glu Arg Phe Gly Pro Ser His
            355                 360                 365

Met Ala Phe Leu Val Val Pro Met Val Gly Ala Phe Phe Ile Asp Ile
        370                 375                 380

Val Asn Ala Leu Val Ile Lys Leu Tyr Leu Met Leu Pro Ile Phe Ala
385                 390                 395                 400

Gly

<210> SEQ ID NO 5
<211> LENGTH: 948
<212> TYPE: DNA
<213> ORGANISM: Escherichia coli
<220> FEATURE:
<221> NAME/KEY: CDS
<222> LOCATION: (1)..(948)

<400> SEQUENCE: 5 gtg tgt cat cgc gca ttt cga ctt cat ctt tgc aag gac tgg gtt ttc      48
Val Cys His Arg Ala Phe Arg Leu His Leu Cys Lys Asp Trp Val Phe
1               5                   10                  15 atg ttt tct ggg ctg tta atc att ctg gtt ccc ctg att gtg ggt tac      96
Met Phe Ser Gly Leu Leu Ile Ile Leu Val Pro Leu Ile Val Gly Tyr
            20                  25                  30 ctc att ccg ctt cgc caa caa gct gcg tta aaa gtt att aat cag cta     144
Leu Ile Pro Leu Arg Gln Gln Ala Ala Leu Lys Val Ile Asn Gln Leu
        35                  40                  45 tta agc tgg atg gtt tac ctt att ctc ttt ttt atg ggt atc agt ctg     192
Leu Ser Trp Met Val Tyr Leu Ile Leu Phe Phe Met Gly Ile Ser Leu
    50                  55                  60 gcg ttt ctc gat aac ctc gcc agt aac ctg ttg gcg att ctg cat tat     240
Ala Phe Leu Asp Asn Leu Ala Ser Asn Leu Leu Ala Ile Leu His Tyr
65                  70                  75                  80 tct gcc gtc agt att acc gtt att tta ctg tgt aat att gcc gcc ctg     288
```

```
Ser Ala Val Ser Ile Thr Val Ile Leu Leu Cys Asn Ile Ala Ala Leu
                    85                  90                  95 atg tgg ctg gag cga ggc ctg ccg tgg cgc aac cac cat cag caa gaa      336
Met Trp Leu Glu Arg Gly Leu Pro Trp Arg Asn His His Gln Gln Glu
                100                 105                 110 aaa ctc ccg tcg cgt att gcg atg gcg ctg gag tcg cta aaa ctg tgc      384
Lys Leu Pro Ser Arg Ile Ala Met Ala Leu Glu Ser Leu Lys Leu Cys
            115                 120                 125 ggc gta gta gtg att ggt ttt gcc att ggt cta agt gga ctg gct ttc      432
Gly Val Val Val Ile Gly Phe Ala Ile Gly Leu Ser Gly Leu Ala Phe
        130                 135                 140 tta caa cac gcg acc gaa gcc agt gaa tac acg tta att ttg cta ctt      480
Leu Gln His Ala Thr Glu Ala Ser Glu Tyr Thr Leu Ile Leu Leu Leu
145                 150                 155                 160 ttc ctc gtt ggt att cag ttg cgc aat aat ggc atg acc tta aag cag      528
Phe Leu Val Gly Ile Gln Leu Arg Asn Asn Gly Met Thr Leu Lys Gln
                165                 170                 175 att gtc ctt aat cgc cgg gga atg att gtc gcc gtg gtg gtg gtt gtc      576
Ile Val Leu Asn Arg Arg Gly Met Ile Val Ala Val Val Val Val Val
                180                 185                 190 agt tca tta att ggt ggt tta att aac gcc ttt att ctt gat ctc ccc      624
Ser Ser Leu Ile Gly Gly Leu Ile Asn Ala Phe Ile Leu Asp Leu Pro
            195                 200                 205 atc aat acc gcg ctg gca atg gcc tcc ggt ttc ggc tgg tat tct ctt      672
Ile Asn Thr Ala Leu Ala Met Ala Ser Gly Phe Gly Trp Tyr Ser Leu
        210                 215                 220 tcc ggt att tta ttg acc gaa tct ttt ggt ccg gta atc ggg agc gcg      720
Ser Gly Ile Leu Leu Thr Glu Ser Phe Gly Pro Val Ile Gly Ser Ala
225                 230                 235                 240 gcg ttt ttt aat gat ctg gcc cgt gaa ctg att gct att atg ttg atc      768
Ala Phe Phe Asn Asp Leu Ala Arg Glu Leu Ile Ala Ile Met Leu Ile
                245                 250                 255 cct ggg ctg att cgc cgc agc cgc tct act gca ctg ggc tta tgc ggt      816
Pro Gly Leu Ile Arg Arg Ser Arg Ser Thr Ala Leu Gly Leu Cys Gly
                260                 265                 270 gcc aca tca atg gat ttc acc ctg ccc gtt ctt caa cgt act ggc ggg      864
Ala Thr Ser Met Asp Phe Thr Leu Pro Val Leu Gln Arg Thr Gly Gly
            275                 280                 285 ctg gat atg gtc ccg gcg gca att gtt cac ggt ttt att ctt agc ctg      912
Leu Asp Met Val Pro Ala Ala Ile Val His Gly Phe Ile Leu Ser Leu
        290                 295                 300 tta gtg ccg atc ctc atc gcc ttt ttc tct gcg taa                      948
Leu Val Pro Ile Leu Ile Ala Phe Phe Ser Ala
305                 310                 315

<210> SEQ ID NO 6
<211> LENGTH: 315
<212> TYPE: PRT
<213> ORGANISM: Escherichia coli

<400> SEQUENCE: 6

Val Cys His Arg Ala Phe Arg Leu His Leu Cys Lys Asp Trp Val Phe
1               5                   10                  15

Met Phe Ser Gly Leu Leu Ile Ile Leu Val Pro Leu Ile Val Gly Tyr
                20                  25                  30

Leu Ile Pro Leu Arg Gln Gln Ala Ala Leu Lys Val Ile Asn Gln Leu
            35                  40                  45

Leu Ser Trp Met Val Tyr Leu Ile Leu Phe Phe Met Gly Ile Ser Leu
        50                  55                  60

Ala Phe Leu Asp Asn Leu Ala Ser Asn Leu Leu Ala Ile Leu His Tyr
```

|  |  |  |  | 65 |  |  |  | 70 |  |  |  | 75 |  |  |  | 80 |
|---|---|---|---|---|---|---|---|---|---|---|---|---|---|---|---|---|
Ser Ala Val Ser Ile Thr Val Ile Leu Leu Cys Asn Ile Ala Ala Leu
              85                        90                      95

Met Trp Leu Glu Arg Gly Leu Pro Trp Arg Asn His His Gln Gln Glu
          100                    105                  110

Lys Leu Pro Ser Arg Ile Ala Met Ala Leu Glu Ser Leu Lys Leu Cys
      115                    120                  125

Gly Val Val Val Ile Gly Phe Ala Ile Gly Leu Ser Gly Leu Ala Phe
    130                    135                  140

Leu Gln His Ala Thr Glu Ala Ser Glu Tyr Thr Leu Ile Leu Leu Leu
145                  150                  155            160

Phe Leu Val Gly Ile Gln Leu Arg Asn Asn Gly Met Thr Leu Lys Gln
              165                  170              175

Ile Val Leu Asn Arg Arg Gly Met Ile Val Ala Val Val Val Val Val
        180                    185                  190

Ser Ser Leu Ile Gly Gly Leu Ile Asn Ala Phe Ile Leu Asp Leu Pro
    195                    200                  205

Ile Asn Thr Ala Leu Ala Met Ala Ser Gly Phe Gly Trp Tyr Ser Leu
210                  215                  220

Ser Gly Ile Leu Leu Thr Glu Ser Phe Gly Pro Val Ile Gly Ser Ala
225                  230                235            240

Ala Phe Phe Asn Asp Leu Ala Arg Glu Leu Ile Ala Ile Met Leu Ile
              245                  250              255

Pro Gly Leu Ile Arg Arg Ser Arg Ser Thr Ala Leu Gly Leu Cys Gly
        260                    265                  270

Ala Thr Ser Met Asp Phe Thr Leu Pro Val Leu Gln Arg Thr Gly Gly
    275                    280                  285

Leu Asp Met Val Pro Ala Ala Ile Val His Gly Phe Ile Leu Ser Leu
290                  295                  300

Leu Val Pro Ile Leu Ile Ala Phe Phe Ser Ala
305                  310                  315

<210> SEQ ID NO 7
<211> LENGTH: 118
<212> TYPE: DNA
<213> ORGANISM: Artificial Sequence
<220> FEATURE:
<223> OTHER INFORMATION: tac promoter and lac RBS

<400> SEQUENCE: 7
tgaagcctgc ttttttatac taacttgagc gagatctccc tgttgacaat taatcatcgg    60
ctcgtataat gtgtggaatc gtgagcggat aacaatttca cacaggaga ctgccatg     118

<210> SEQ ID NO 8
<211> LENGTH: 35
<212> TYPE: DNA
<213> ORGANISM: Artificial Sequence
<220> FEATURE:
<223> OTHER INFORMATION: primer

<400> SEQUENCE: 8
cattaatgca gcgaaaagct ctgttgttaa agggt                               35

<210> SEQ ID NO 9
<211> LENGTH: 24
<212> TYPE: DNA
<213> ORGANISM: Artificial Sequence
<220> FEATURE:
<223> OTHER INFORMATION: primer

```
<400> SEQUENCE: 9
ggcgtaggcc tgataagacg cggc                                              24

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
ggcattttag ctgaccgaaa g                                                 21

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
tcacgaacgt tacccacaac                                                   20

<210> SEQ ID NO 12
<211> LENGTH: 437
<212> TYPE: PRT
<213> ORGANISM: Artificial Sequence
<220> FEATURE:
<223> OTHER INFORMATION: consensus
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (28)..(31)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (37)..(38)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
```

```
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (97)..(98)
<223> OTHER INFORMATION: Xaa can be any naturally occurring amino acid
<220> FEATURE:
<221> NAME/KEY: misc_feature
<222> LOCATION: (110)..(110)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid
<220> FEATURE:
<221> NAME/KEY: misc_feature
<222> LOCATION: (119)..(119)
<223> OTHER INFORMATION: Xaa can be any naturally occurring amino acid
<220> FEATURE:
<221> NAME/KEY: misc_feature
<222> LOCATION: (127)..(127)
<223> OTHER INFORMATION: Xaa can be any naturally occurring amino acid
<220> FEATURE:
<221> NAME/KEY: misc_feature
<222> LOCATION: (130)..(131)
<223> OTHER INFORMATION: Xaa can be any naturally occurring amino acid
<220> FEATURE:
<221> NAME/KEY: misc_feature
<222> LOCATION: (135)..(136)
<223> OTHER INFORMATION: Xaa can be any naturally occurring amino acid
<220> FEATURE:
<221> NAME/KEY: misc_feature
<222> LOCATION: (139)..(139)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (159)..(159)
<223> OTHER INFORMATION: Xaa can be any naturally occurring amino acid
<220> FEATURE:
<221> NAME/KEY: misc_feature
<222> LOCATION: (180)..(180)
<223> OTHER INFORMATION: Xaa can be any naturally occurring amino acid
<220> FEATURE:
<221> NAME/KEY: misc_feature
<222> LOCATION: (192)..(192)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (216)..(216)
<223> OTHER INFORMATION: Xaa can be any naturally occurring amino acid
<220> FEATURE:
<221> NAME/KEY: misc_feature
<222> LOCATION: (221)..(221)
<223> OTHER INFORMATION: Xaa can be any naturally occurring amino acid
<220> FEATURE:
<221> NAME/KEY: misc_feature
<222> LOCATION: (225)..(225)
<223> OTHER INFORMATION: Xaa can be any naturally occurring amino acid
<220> FEATURE:
<221> NAME/KEY: misc_feature
<222> LOCATION: (235)..(235)
<223> OTHER INFORMATION: Xaa can be any naturally occurring amino acid
<220> FEATURE:
<221> NAME/KEY: misc_feature
<222> LOCATION: (238)..(239)
<223> OTHER INFORMATION: Xaa can be any naturally occurring amino acid
```

```
<220> FEATURE:
<221> NAME/KEY: misc_feature
<222> LOCATION: (242)..(242)
<223> OTHER INFORMATION: Xaa can be any naturally occurring amino acid
<220> FEATURE:
<221> NAME/KEY: misc_feature
<222> LOCATION: (247)..(247)
<223> OTHER INFORMATION: Xaa can be any naturally occurring amino acid
<220> FEATURE:
<221> NAME/KEY: misc_feature
<222> LOCATION: (251)..(251)
<223> OTHER INFORMATION: Xaa can be any naturally occurring amino acid
<220> FEATURE:
<221> NAME/KEY: misc_feature
<222> LOCATION: (255)..(255)
<223> OTHER INFORMATION: Xaa can be any naturally occurring amino acid
<220> FEATURE:
<221> NAME/KEY: misc_feature
<222> LOCATION: (259)..(260)
<223> OTHER INFORMATION: Xaa can be any naturally occurring amino acid
<220> FEATURE:
<221> NAME/KEY: misc_feature
<222> LOCATION: (262)..(262)
<223> OTHER INFORMATION: Xaa can be any naturally occurring amino acid
<220> FEATURE:
<221> NAME/KEY: misc_feature
<222> LOCATION: (269)..(269)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid
<220> FEATURE:
<221> NAME/KEY: misc_feature
<222> LOCATION: (298)..(298)
<223> OTHER INFORMATION: Xaa can be any naturally occurring amino acid
<220> FEATURE:
<221> NAME/KEY: misc_feature
<222> LOCATION: (334)..(334)
<223> OTHER INFORMATION: Xaa can be any naturally occurring amino acid
<220> FEATURE:
<221> NAME/KEY: misc_feature
<222> LOCATION: (337)..(338)
<223> OTHER INFORMATION: Xaa can be any naturally occurring amino acid
<220> FEATURE:
<221> NAME/KEY: misc_feature
<222> LOCATION: (342)..(342)
<223> OTHER INFORMATION: Xaa can be any naturally occurring amino acid
<220> FEATURE:
<221> NAME/KEY: misc_feature
<222> LOCATION: (358)..(358)
<223> OTHER INFORMATION: Xaa can be any naturally occurring amino acid
<220> FEATURE:
<221> NAME/KEY: misc_feature
<222> LOCATION: (409)..(409)
<223> OTHER INFORMATION: Xaa can be any naturally occurring amino acid
<220> FEATURE:
<221> NAME/KEY: misc_feature
<222> LOCATION: (414)..(414)
<223> OTHER INFORMATION: Xaa can be any naturally occurring amino acid
<220> FEATURE:
<221> NAME/KEY: misc_feature
<222> LOCATION: (421)..(421)
<223> OTHER INFORMATION: Xaa can be any naturally occurring amino acid
<220> FEATURE:
<221> NAME/KEY: misc_feature
<222> LOCATION: (426)..(427)
<223> OTHER INFORMATION: Xaa can be any naturally occurring amino acid
<220> FEATURE:
<221> NAME/KEY: misc_feature
<222> LOCATION: (430)..(430)
<223> OTHER INFORMATION: Xaa can be any naturally occurring amino acid
<220> FEATURE:
<221> NAME/KEY: misc_feature
<222> LOCATION: (433)..(433)
<223> OTHER INFORMATION: Xaa can be any naturally occurring amino acid
<220> FEATURE:
<221> NAME/KEY: misc_feature
<222> LOCATION: (436)..(436)
<223> OTHER INFORMATION: Xaa can be any naturally occurring amino acid
```

<400> SEQUENCE: 12

```
Met Lys Xaa Xaa Lys Xaa Ser Leu Ala Trp Gln Ile Leu Xaa Ala Xaa
1               5                   10                  15

Val Leu Gly Ile Leu Leu Gly Ser Xaa Leu His Xaa Xaa Xaa Xaa Ser
            20                  25                  30

Arg Xaa Trp Leu Xaa Xaa Asn Xaa Leu Xaa Pro Ala Gly Asp Ile Phe
        35                  40                  45

Ile His Leu Ile Lys Met Ile Val Pro Ile Val Ile Ser Thr Leu
    50                  55                  60

Xaa Val Gly Ile Ala Gly Val Gly Asp Ala Lys Gln Leu Gly Arg Ile
65                  70                  75                  80

Gly Ala Lys Thr Ile Xaa Tyr Phe Glu Xaa Ile Thr Thr Val Ala Ile
                85                  90                  95

Xaa Xaa Gly Ile Thr Leu Ala Asn Val Phe Gln Pro Gly Xaa Gly Xaa
                100                 105                 110

Asp Met Ser Gln Leu Ala Xaa Val Asp Ile Ser Lys Tyr Gln Xaa Thr
            115                 120                 125

Thr Xaa Xaa Val Gln Ser Xaa Xaa His Gly Xaa Met Gly Thr Ile Leu
    130                 135                 140

Ser Leu Val Pro Thr Asn Ile Xaa Ala Ser Met Ala Lys Gly Xaa Met
145                 150                 155                 160

Leu Pro Ile Ile Phe Phe Ser Val Leu Phe Gly Leu Gly Leu Ser Ser
                165                 170                 175

Leu Pro Ala Xaa His Arg Glu Pro Leu Val Thr Val Phe Arg Ser Xaa
            180                 185                 190

Ser Glu Thr Met Phe Lys Val Thr His Met Val Met Arg Tyr Ala Pro
        195                 200                 205

Val Gly Val Phe Xaa Leu Ile Xaa Val Thr Val Ala Xaa Phe Gly Phe
    210                 215                 220

Xaa Ser Leu Trp Pro Leu Ala Lys Leu Val Xaa Leu Val Xaa Xaa Ala
225                 230                 235                 240

Ile Xaa Phe Phe Ala Leu Xaa Val Leu Gly Xaa Val Ala Arg Xaa Cys
                245                 250                 255

Gly Leu Xaa Xaa Trp Xaa Leu Ile Arg Ile Leu Lys Xaa Glu Leu Ile
            260                 265                 270

Leu Ala Tyr Ser Thr Ala Ser Ser Glu Ser Val Leu Xaa Arg Ile Ile
        275                 280                 285

Glu Lys Met Glu Ala Tyr Gly Ala Pro Xaa Ser Ile Thr Ser Phe Val
290                 295                 300

Val Pro Thr Gly Tyr Ser Phe Asn Leu Asp Gly Ser Thr Leu Tyr Gln
305                 310                 315                 320

Ser Ile Ala Ala Ile Phe Ile Ala Gln Leu Tyr Gly Ile Xaa Leu Ser
            325                 330                 335

Xaa Xaa Gln Glu Ile Xaa Leu Val Leu Thr Leu Met Val Thr Ser Lys
        340                 345                 350

Gly Ile Ala Gly Val Xaa Gly Val Ser Phe Val Val Leu Leu Ala Thr
            355                 360                 365

Leu Gly Ser Val Gly Ile Pro Leu Glu Gly Leu Ala Phe Ile Ala Gly
    370                 375                 380

Val Asp Arg Ile Leu Asp Met Ala Arg Thr Ala Leu Asn Val Val Gly
385                 390                 395                 400

Asn Ala Leu Ala Val Leu Val Ile Xaa Lys Trp Glu His Xaa Phe Asp
                405                 410                 415
```

```
Arg Lys Lys Ala Xaa Ala Tyr Glu Arg Xaa Xaa Leu Gly Xaa Phe Asp
            420                 425                 430

Xaa Thr Ala Xaa Gln
        435

<210> SEQ ID NO 13
<211> LENGTH: 401
<212> TYPE: PRT
<213> ORGANISM: Artificial Sequence
<220> FEATURE:
<223> OTHER INFORMATION: consensus
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
```

```
<222> LOCATION: (145)..(145)
<223> OTHER INFORMATION: Xaa can be any naturally occurring amino acid
<220> FEATURE:
<221> NAME/KEY: misc_feature
<222> LOCATION: (149)..(149)
<223> OTHER INFORMATION: Xaa can be any naturally occurring amino acid
<220> FEATURE:
<221> NAME/KEY: misc_feature
<222> LOCATION: (155)..(156)
<223> OTHER INFORMATION: Xaa can be any naturally occurring amino acid
<220> FEATURE:
<221> NAME/KEY: misc_feature
<222> LOCATION: (176)..(176)
<223> OTHER INFORMATION: Xaa can be any naturally occurring amino acid
<220> FEATURE:
<221> NAME/KEY: misc_feature
<222> LOCATION: (191)..(191)
<223> OTHER INFORMATION: Xaa can be any naturally occurring amino acid
<220> FEATURE:
<221> NAME/KEY: misc_feature
<222> LOCATION: (193)..(193)
<223> OTHER INFORMATION: Xaa can be any naturally occurring amino acid
<220> FEATURE:
<221> NAME/KEY: misc_feature
<222> LOCATION: (198)..(198)
<223> OTHER INFORMATION: Xaa can be any naturally occurring amino acid
<220> FEATURE:
<221> NAME/KEY: misc_feature
<222> LOCATION: (242)..(243)
<223> OTHER INFORMATION: Xaa can be any naturally occurring amino acid
<220> FEATURE:
<221> NAME/KEY: misc_feature
<222> LOCATION: (247)..(247)
<223> OTHER INFORMATION: Xaa can be any naturally occurring amino acid
<220> FEATURE:
<221> NAME/KEY: misc_feature
<222> LOCATION: (263)..(265)
<223> OTHER INFORMATION: Xaa can be any naturally occurring amino acid
<220> FEATURE:
<221> NAME/KEY: misc_feature
<222> LOCATION: (293)..(293)
<223> OTHER INFORMATION: Xaa can be any naturally occurring amino acid
<220> FEATURE:
<221> NAME/KEY: misc_feature
<222> LOCATION: (312)..(312)
<223> OTHER INFORMATION: Xaa can be any naturally occurring amino acid
<220> FEATURE:
<221> NAME/KEY: misc_feature
<222> LOCATION: (362)..(362)
<223> OTHER INFORMATION: Xaa can be any naturally occurring amino acid
<220> FEATURE:
<221> NAME/KEY: misc_feature
<222> LOCATION: (378)..(378)
<223> OTHER INFORMATION: Xaa can be any naturally occurring amino acid
<220> FEATURE:
<221> NAME/KEY: misc_feature
<222> LOCATION: (395)..(395)
<223> OTHER INFORMATION: Xaa can be any naturally occurring amino acid
<220> FEATURE:
<221> NAME/KEY: misc_feature
<222> LOCATION: (398)..(398)
<223> OTHER INFORMATION: Xaa can be any naturally occurring amino acid
<220> FEATURE:
<221> NAME/KEY: misc_feature
<222> LOCATION: (400)..(400)
<223> OTHER INFORMATION: Xaa can be any naturally occurring amino acid

<400> SEQUENCE: 13

Met Phe Xaa Leu Asp Thr Leu Xaa Thr Leu Val Ala Ala Thr Leu Xaa
1               5                   10                  15

Leu Leu Leu Gly Arg Lys Leu Val Xaa Ser Val Ser Xaa Leu Lys Lys
            20                  25                  30

Tyr Thr Ile Pro Glu Pro Val Ala Gly Gly Leu Leu Val Ala Xaa Ala
        35                  40                  45

Leu Leu Xaa Leu Lys Lys Ser Xaa Gly Trp Glu Val Asn Phe Asp Met
    50                  55                  60
```

Xaa Leu Arg Asp Pro Leu Met Leu Ala Phe Phe Ala Thr Ile Gly Leu
 65                  70                  75                  80

Asn Ala Asn Xaa Ala Xaa Leu Arg Xaa Gly Gly Arg Val Val Gly Xaa
                 85                  90                  95

Phe Leu Xaa Val Val Gly Leu Leu Xaa Met Gln Asn Ala Ile Gly
            100                 105                 110

Ile Gly Met Ala Ser Leu Leu Gly Leu Asp Pro Leu Met Gly Leu Xaa
            115                 120                 125

Ala Gly Ser Ile Thr Leu Ser Gly Gly His Gly Thr Gly Ala Ala Trp
130                 135                 140

Xaa Lys Leu Phe Xaa Glu Arg Tyr Gly Phe Xaa Xaa Ala Thr Glu Val
145                 150                 155                 160

Ala Met Ala Cys Ala Thr Phe Gly Leu Val Leu Gly Gly Leu Ile Xaa
                165                 170                 175

Gly Pro Val Ala Arg Tyr Leu Val Lys His Ser Thr Thr Pro Xaa Gly
            180                 185                 190

Xaa Pro Asp Asp Gln Xaa Val Pro Thr Ala Phe Glu Lys Pro Asp Val
            195                 200                 205

Gly Arg Met Ile Thr Ser Leu Val Leu Ile Glu Thr Ile Ala Leu Ile
210                 215                 220

Ala Ile Cys Leu Thr Val Gly Lys Ile Val Ala Gln Leu Leu Ala Gly
225                 230                 235                 240

Thr Xaa Xaa Glu Leu Pro Xaa Phe Val Cys Val Leu Phe Val Gly Val
            245                 250                 255

Ile Leu Ser Asn Gly Leu Xaa Xaa Xaa Gly Phe Tyr Arg Val Phe Glu
            260                 265                 270

Arg Ala Val Ser Val Leu Gly Asn Val Ser Leu Ser Leu Phe Leu Ala
            275                 280                 285

Met Ala Leu Met Xaa Leu Lys Leu Trp Glu Leu Ala Ser Leu Ala Leu
290                 295                 300

Pro Met Leu Ala Ile Leu Val Xaa Gln Thr Ile Phe Met Ala Leu Tyr
305                 310                 315                 320

Ala Ile Phe Val Thr Trp Arg Met Met Gly Lys Asn Tyr Asp Ala Ala
                325                 330                 335

Val Leu Ala Ala Gly His Cys Gly Phe Gly Leu Gly Ala Thr Pro Thr
            340                 345                 350

Ala Ile Ala Asn Met Gln Ala Ile Thr Xaa Arg Phe Gly Pro Ser His
            355                 360                 365

Met Ala Phe Leu Val Val Pro Met Val Xaa Ala Phe Phe Ile Asp Ile
370                 375                 380

Val Asn Ala Leu Val Ile Lys Leu Tyr Leu Xaa Leu Pro Xaa Phe Xaa
385                 390                 395                 400

Gly

<210> SEQ ID NO 14
<211> LENGTH: 35
<212> TYPE: DNA
<213> ORGANISM: Artificial Sequence
<220> FEATURE:
<223> OTHER INFORMATION: primer

<400> SEQUENCE: 14
tacccgggta atatggctac atcagtacag acagg                                35

<210> SEQ ID NO 15

```
<211> LENGTH: 26
<212> TYPE: DNA
<213> ORGANISM: Artificial Sequence
<220> FEATURE:
<223> OTHER INFORMATION: primer

<400> SEQUENCE: 15 gagagctcaattatcgctcccttgtc                                              26
```